US009086399B2

(12) United States Patent
Dorr et al.

(10) Patent No.: US 9,086,399 B2
(45) Date of Patent: Jul. 21, 2015

(54) DIAGNOSTIC SYSTEM AND DIAGNOSING METHOD, HOUSING COMPONENT OF A LUBRICANT CONTAINER

(71) Applicant: Airbus Operations GmbH, Hamburg (DE)

(72) Inventors: Björn Dorr, Stuhr (DE); Franz Nuscheler, München (DE); Sumit Paul, München (DE)

(73) Assignee: Airbus Operations GmbH, Hamburg (DE)

( * ) Notice: Subject to any disclaimer, the term of this patent is extended or adjusted under 35 U.S.C. 154(b) by 137 days.

(21) Appl. No.: 13/866,335

(22) Filed: Apr. 19, 2013

(65) Prior Publication Data

US 2013/0304312 A1 Nov. 14, 2013

Related U.S. Application Data

(63) Continuation of application No. PCT/EP2011/005274, filed on Oct. 19, 2011.

(60) Provisional application No. 61/394,482, filed on Oct. 19, 2010.

(30) Foreign Application Priority Data

Oct. 19, 2010 (DE) .......................... 10 2010 048 950

(51) Int. Cl.
| | |
|---|---|
| H03M 1/08 | (2006.01) |
| F01M 11/12 | (2006.01) |
| G01N 33/28 | (2006.01) |
| H04Q 9/00 | (2006.01) |

(52) U.S. Cl.
CPC .......... *G01N 33/2888* (2013.01); *F01M 11/12* (2013.01); *H03M 1/0854* (2013.01);

(Continued)

(58) Field of Classification Search
CPC ............... G01N 33/2888; F01M 11/12; G08C 2201/10; G08C 2201/51; H04Q 9/00; H04Q 2209/75; H04Q 2209/883; H03M 1/0854
USPC ........................................................ 701/34.4
See application file for complete search history.

(56) References Cited

U.S. PATENT DOCUMENTS

| | | | | |
|---|---|---|---|---|
| 6,557,396 | B2* | 5/2003 | Ismail et al. ................. | 73/53.05 |
| 6,750,763 | B2* | 6/2004 | Ismail et al. ............... | 340/450.3 |
| 2006/0105467 | A1 | 5/2006 | Niksa | |

FOREIGN PATENT DOCUMENTS

| | | |
|---|---|---|
| DE | 101 20 015 | 11/2001 |
| DE | 101 53 151 | 5/2003 |

(Continued)

OTHER PUBLICATIONS

International Search Report for Application No. PCT/EP 2011/005274 dated Jan. 23, 2012.

*Primary Examiner* — Richard Camby
(74) *Attorney, Agent, or Firm* — Jenkins, Wilson, Taylor & Hunt, P.A.

(57) ABSTRACT

Diagnostic system including a sensor device with a sensor for generating signals corresponding to a first operational condition, a control device with a timer and function for performance of measurements, and a signal transmission device. The system includes a device for determination of a second operational condition of the system component and configured where the sensor value of the signal transmission device corresponding to the first operational condition is furnished when the sensor value corresponding to a second operational condition of the transmission mechanism is higher or lower than a comparative value, and housing component of a lubricant container and in particular closure device for sealing an opening of such a housing component from a lubricant which is present in the operational use thereof in an internal space thereof, having arranged therein: at least one sensor device comprising at least one sensor for determining the water content in the lubricant.

6 Claims, 5 Drawing Sheets

(52) U.S. Cl.
CPC .............. *H04Q 9/00* (2013.01); *G08C 2201/10* (2013.01); *G08C 2201/51* (2013.01); *H04Q 2209/75* (2013.01); *H04Q 2209/883* (2013.01)

(56) References Cited

FOREIGN PATENT DOCUMENTS

| DE | 101 53 152 | 5/2003 |
|---|---|---|
| DE | 10 2009 015 654 | 12/2009 |
| DE | 10 2009 036 223 | 5/2010 |
| DE | 10 2009 016 642 | 10/2010 |
| EP | 1008971 | 6/2000 |
| WO | WO 9846984 | 10/1998 |
| WO | WO 01/90539 | 11/2001 |
| WO | WO 02/31323 | 4/2002 |
| WO | WO 2008/141035 | 11/2008 |
| WO | WO 2010/095075 | 8/2010 |
| WO | WO 2012/052168 | 4/2012 |

* cited by examiner

DIAGNOSTIC SYSTEM AND DIAGNOSING METHOD, HOUSING COMPONENT OF A LUBRICANT CONTAINER

CROSS-REFERENCE TO RELATED APPLICATIONS

This application is a continuation of and claims priority to PCT Application No. PCT/EP2011/005274, filed Oct. 19, 2011, which claims the benefit of the filing date of German Application Serial No. DE 10 2010 048 950.6, filed Oct. 19, 2010, and of U.S. Provisional Application Ser. No. 61/394,482, filed Oct. 19, 2010, the disclosures of which applications are incorporated by reference herein.

TECHNICAL FIELD

The invention relates to a diagnostic system and a diagnosing method in particular for monitoring the operational condition of a lubricant in the lubricant container, a housing component and in particular a closure device for such a housing component, as well as a lubricant container.

The invention relates in particular to a housing part partially or entirely constituting a lubricant container for partially or entirely receiving a power transmission mechanism which includes at least one inlet and/or outlet opening for filling and draining a lubricant into and from the housing part, wherein the inlet and outlet openings are sealed by means of releasable closure devices.

BACKGROUND

The like housing parts comprising a lubricant reservoir are used for installation into land, air, water or underwater vehicles and serve there for receiving movable mechanical components such as particularly transmissions or rotary actuators, wherein these movable components are bathed in the lubricating fluid accommodated in the lubricant reservoir of the housing part, whereby they are lubricated and also cooled in a given case.

From DE 101 53 152 A1 a system and a method for the maintenance of actuators of aircraft by using sensors for measuring the humidity content in the actuators are known.

SUMMARY

It is an object of the invention to provide a housing component and in particular a closure device or a housing part for a lubricant container, a lubricant container of this kind, a diagnostic system, and a diagnosing method for monitoring the operational condition of a lubricant in the lubricant container, whereby it is possible to efficiently detect or monitor the operational condition of lubricant used in mechanical apparatus such as, e.g., actuators.

This object is achieved through the features of the independent claims. Further embodiments are specified in the subclaims appended to them.

The solution in accordance with the invention allows in particular to monitor the effects of extreme fluctuations of the external environmental conditions to which such housing parts on vehicles are exposed in practical use, which may bring about an undesirable inclusion of condensed water in the lubricant reservoir or other undesirable reactions of the lubricant, and which may negatively influence the consistency of the lubricant composition.

By way of example, this set of problems is explained in more detail in the following by making reference to components that are installed in the high lift system of an aircraft:

The high lift system of an aircraft is made up of numerous system components that are for the most part, due to their placement, directly exposed to the environmental conditions. During variations of altitude (i.e., climb or descent) the environmental conditions such as external temperature, external air pressure and atmospheric humidity are subject to change. Hermetic sealing is not possible for most system components and thus also for the rotary actuators in the high lift system, for which reason dynamic seals are frequently employed.

Such seals are, however, not capable of preventing temperature, air pressure and atmospheric humidity from varying all the time within the system components. Depending on climbing rate and sink rate, however, these variations occur more or less at a time delay from the variations of the environmental conditions. This means that during the climb the air pressure within a system component will always be somewhat higher than the outside air pressure, and during the descent the air pressure within the system component will generally be somewhat lower than the outside air pressure.

An increased pressure consequently acts on the component during the landing approach, so that—especially in (tropical and subtropical) regions of high atmospheric humidity—condensed water forms inside the system components. While the high lift system of an aircraft is being extended, rotary actuators are driven via a transmission shaft system. The actuators contain lubricant of the semifluid type (semifluid low-viscosity greases). If the gears inside the actuator are caused to move during an adjustment of the high lift flaps while condensed water has entered into the actuators, the semifluid mixes with the penetrated water. This process repeats itself with an increasing number of flights, so that the water content in the semifluid increases. From a certain degree of humidity the low temperatures at cruising altitude bring about the risk of ice forming in the actuator, which may in the worst case result in jamming while the flaps are being extended. Should this scenario occur, the high lift system would not be available to the pilot any more during the landing approach.

Previously this problem was generally dealt with by regularly replacing the semifluid while observing certain maintenance intervals. For maintenance, initially the shut-off screws on the housing part are removed, after which the semifluid may drain through the lower outlet. Once semifluid ceases to flow out, the lower shut-off screw together with the sealing washer is mounted again. Then a hose, the second end of which leads into a collecting receptacle, is fixed at the upper outlet opening. Following removal of the shut-off screw, the new semifluid may be supplied via the inlet valve with the aid of a grease gun. Following successful filling with the fixed filling quantity, the inlet and outlet openings are closed by means of the corresponding shut-off screws. If the maintenance intervals are not observed, or in the event of an elevated degree of humidity, the semifluid becomes increasingly more viscous, in which case a replacement will only be possible by opening the housing lid. In that case, however, the maintenance effort is so time-consuming that a full replacement of the housing part will frequently be effected for economic reasons. From the maintenance point of view it is a drawback of this known manner of proceeding that the semifluid must be replaced at regular intervals in the above-described manner in order to avoid jamming. As the water content in the semifluid increases at different rates in dependence on the flight route, it would be necessary under an economic viewpoint to separately determine the optimum time for a semifluid exchange for each aircraft. This prediction is extremely difficult, however, for which reason the semifluid is replaced at fixed maintenance intervals.

If maintenance is performed prematurely, with the humidity or water proportion amounting to only a few percent, the airline company might have saved the costs for the maintenance. If excessively long maintenance intervals are selected, the airline company risks damage to partial components or even jamming in the actuator, while an elevated degree of humidity may moreover cause the semifluid to become so viscous that it is not possible any more to replace the semifluid without a time-consuming and thus costly operation of opening the rotary actuator—mostly ending up in the component being replaced.

The solution in accordance with the invention allows to avoid or clearly limit the maintenance expenditure described in the foregoing in general for vehicles comprising transmission mechanisms that are lubricated with a lubricant. Aside from the use of the solution in accordance with the invention as described for a flap rotary actuator for the adjustment of a flap (landing flap) on the wing of an aircraft for monitoring the inclusion of condensed water in this flap rotary actuator, the solution in accordance with the invention may also be provided similarly on any kind of housing parts having movable mechanical components in a lubricant reservoir in any land, air, water or underwater vehicles (e.g., automotive vehicles, aircraft, helicopters, ships, submarines, etc.). The use of the solution in accordance with the invention may particularly be provided where undesirable variations of the composition and properties of the lubricant may occur during use of such a vehicle owing to external environmental influences, so that the lubricant composition must be monitored regularly and the lubricant must in a given case be replaced in due time. The invention may thus generally be provided for housing parts intended for installation in a vehicle and having movable components mounted therein inside a lubricant reservoir such as, e.g., transmissions or rotary actuators. What is proposed is a structure wherein a regular diagnosis of the consistency of the lubricant being exposed to external environmental influences may be carried out in the most simple way possible, and that, when such diagnosis yields the result that a replacement of the lubricant has to be effected, the replacement operation may be carried out in the most simple way possible. In addition a diagnostic system and a diagnosing method are provided which allow the most simple monitoring possible of the operational condition of the lubricant in the lubricant reservoir inside a housing part including movable mechanical components.

What is provided in accordance with the invention is a housing component of a lubricant container and in particular a closure device for sealing an opening of such a housing component from a lubricant present during the operational use thereof in an internal space of the lubricant container, the housing component comprising:

at least one sensor device comprising at least one sensor for generating sensor signals corresponding to the respective operational condition and in particular the water content of the lubricant, wherein the at least one sensor is disposed on a portion which faces the inside of the housing part during insertion of the closure device in order to be placed in contact with the lubricant, at least one transceiver for receiving the sensor signals from the sensor device and for signal transmission of the sensor signals to an external reception unit, in a given case a power supply device for supplying electric power to the sensor device and to the transceiver, wherein the at least one sensor for determining the water content in the lubricant is realized as a capacitor having capacitor electrodes, and the surface of at least one of the capacitor electrodes is coated in portions thereof with a protective layer.

The surface of only one electrode of the capacitor may also be coated in portions thereof only. In particular, the protective layer of the housing component may then be formed of Si oxide and/or a Si nitride or, for example, aluminum oxide.

Due to the provision of a sensor device in a closure device, the sensor device comprising the closure device may readily be replaced while a separate and complex integration and control activity is not required for inserting the closure device in the location intended for it, e.g., an opening of a housing part. Moreover the logistic effort for replacement parts for the sensor device is simple as it is readily possible to replace the closure devices.

In accordance with an embodiment in accordance with the invention, the housing component is realized as a closure device. Here the closure device may be realized as a screw and adapted for insertion into a threaded reception of an inlet opening or outlet opening, or as a bolt having a securing element for closing, e.g., a respective inlet opening or an outlet opening by means of the bolt.

According to a further embodiment of the housing component, the latter comprises a function module having a signal transmission device which is functionally communicated with the sensor device so as to be able to transmit measurement values determined by the sensor device to an external reception and/or transmission device. The electrodes may also be realized as antennae.

The transceiver may in particular be adapted for establishing a wireless transmission connection for transmitting the sensor signals to an external reception unit and may be coupled to an antenna or antenna device disposed on a surface of a second end portion situated opposite from the first end portion.

The housing component of the invention and in particular the closure device of the invention may comprise a function module additionally comprising a device for determining the operational condition of the transmission mechanism and in particular a temperature sensor for detecting the temperature of the lubricant and/or a pressure sensor for detecting the pressure of the lubricant. The function module may furthermore be realized such that it only detects a sensor value for the operational condition of the lubricant or only stores a sensor value for the operational condition of the lubricant detected by the sensor device in a memory device and/or only transmits it to the signal transmission device if it is determined with the aid of the device for determining the operational condition that the detected operational condition of the transmission mechanism is above or below a predetermined operational condition of the transmission mechanism.

In particular the function module may comprise a control device which is functionally communicated with the sensor device or with the memory device and which upon reception of a request for transmission of measurement data received from the signal transmission device activates the performance of a measurement by the sensor device, e.g. by means of an activation signal, and supplies at least one detected sensor value from the sensor device or at least one sensor value stored in the memory device to the signal transmission device. Moreover the signal transmission device may be realized in such a way that it transmits the at least one received sensor value to an external reception and/or transmission device.

In another embodiment of the function module the latter is realized such that the control device initiates the measurement of the operational condition in the lubricant or the determination of the operational condition of the transmission mechanism at predetermined time intervals.

In these embodiments the function module may be realized in such a way that it may switch the antenna device between an energy-saving standby mode and an active transmission and/or reception mode, that in the standby mode the transmission and reception module determines at predetermined time intervals whether a minimum signal strength is present as a result of a query by an external reception and/or transmission device, and that based on the determination of such a query by the control device the transmission and reception module transmits information corresponding to this query via the antenna device to the external reception and/or transmission device.

In accordance with one embodiment of the invention it is provided that the function module provides to the signal transmission device the respective most recent measurement value or a predetermined number of most recent measurement values concerning the operational condition of the lubricant.

In accordance with one embodiment of the invention it is provided that the query of the external reception and/or transmission device such as, e.g., a maintenance device is registered as a query with regard to sending of a measurement value or of information concerning the lubricant only if an address specified with the query is identical with a predetermined address stored in the function module.

According to a further aspect of the invention, a function module having the combinations of features described in the foregoing is provided in particular for use in a transmission mechanism.

Moreover it may be provided that the sensor device comprises a sensor and in particular a humidity sensor for detecting the water content of the lubricant and/or a temperature sensor for detecting the temperature of the lubricant and/or a pressure sensor for detecting the pressure of the lubricant and/or the external pressure. In particular a combination of the measurements of the water content or humidity content and of the temperature of the lubricant may be performed, whereby the measurement of the water content may be performed more accurately. In this practical example, the measurement function integrated in the sensor device determines the water content as a function of the equally measured temperature of the lubricant.

According to a further practical example, the sensor device may include a measurement function wherein at least one temporal specification for the performance of a measurement and a function for the performance of the measurement are set up, which measurement function activates the sensor when the temporal specification is satisfied and detects sensor signals for the determination of sensor values. The temporal specification may be realized through a timer of the sensor device which is coupled to the measurement function such that the measurement function carries out a measurement of the operational condition of the lubricant in response to an activation signal of the timer. In this case the measurement value for the operational condition of the lubricant is stored in a memory device from where the measurement value may be read out in response to a query, e.g. by an external maintenance device, and transmitted to the maintenance device. This practical example presents the advantage that the closure device comprising the sensor device may be realized in a very simple manner. The sensor functions for the measurement may moreover be operative independently of external devices such as, e.g., the maintenance device. As a result, the measurement function for performing the measurement particularly does not need to have an interface with an external device.

According to one practical example, the transceiver may alternatively or additionally comprise a driving device which is functionally communicated with the sensor device and activates the measurement function of the sensor device by means of an activation signal in response to reception of a measurement command for performing a measurement, so that the sensor device detects at least one sensor signal for the determination of sensor values and transmits it to the transceiver.

The sensor device may comprise, or be made up of, a planar capacitor which is constituted by two capacitor parts facing each other. Alternatively, the sensor device may comprise a plate capacitor having two capacitor plates. In this case the sensor surface of the first end portion intended for entering into contact with the lubricant may in particular be configured partly as a groove, with two mutually facing surfaces of the side walls of the groove each forming an outer side of a respective one of the capacitor plates. The groove may in particular be an annular groove. In these embodiments it is provided in particular that in order to measure the operational condition of the lubricant, the sensor surface intended for entering into contact with the lubricant is arranged on the closure device in such a way as to face the inside of the housing part when the closure device is in the closing state.

According to a further aspect of the invention, a housing part of a lubricant container is provided which comprises a sensor device according to the invention that is adapted for generating sensor signals corresponding to the operational condition of the lubricant contained in the housing part. In particular it may be provided that the housing part comprises at least one opening and a closure device adapted to be inserted therein and comprising a sensor device in accordance with the invention. The closure device may in particular be realized in accordance with one of the presently described practical examples. The housing part and the closure device may furthermore be configured such that in the state of the closure device in which it closes the housing part, a surface of a first end portion of the closure device faces the interior of the housing part so as to be in contact with the lubricant, wherein the surface is realized as a sensor surface for the detection of the sensor values.

According to a further practical example of the invention it is provided that the housing part has at least one outlet opening or inlet opening for draining the lubricant from the housing or lubricant container in the composite state, the part of which is the housing part, and that the at least one outlet opening or inlet opening, respectively, is sealed by the releasable closure device. The closure device may be realized as a screw, and the respective opening of the housing part may have a threaded reception for receiving the screw. The closure device may moreover be realized as a bolt having a securing element for closing the respective inlet and outlet opening by the bolt. Due to the provision or insertion of a closure device of the invention in an outlet opening or inlet opening of the housing part of a lubricant container, an opening which at any rate is already provided, in a given case for a different purpose, may additionally be provided for the integration of a sensor device of the invention. In this way a separate mechanical integrating effort is not required for integrating the sensor device provided in accordance with the invention in the housing part or in the lubricant container, respectively.

The housing part of the invention constituting a lubricant container may in particular be a housing part of a power transmission mechanism. In particular, the transmission mechanism may be a transmission, or gearing. The transmission may moreover be the transmission of a rotary actuator.

According to a further aspect of the invention a diagnostic system or a maintenance device is provided, comprising: a housing part comprising a sensor device in accordance with one of the practical examples presently described and a transceiver associated thereto, and a maintenance device comprising a transceiver for receiving sensor signals from the transceiver associated to the sensor device. The maintenance device may include a function whereby it may query and receives a measurement value determined by the sensor device concerning the water content of the lubricant contained in the container, wherein the measurement value is a measurement value that was measured at a temperature of the lubricant which is higher than a minimum temperature.

In accordance with the invention there is in particular provided a diagnostic system for detecting and transmitting a sensor value concerning an operational condition of a system component to an external reception and/or transmission device, the diagnostic system comprising:

at least one sensor device comprising at least one sensor for generating sensor signals corresponding to the respective first operational condition, a control device comprising a timer and a function for the performance of measurements by means of the sensor device at predetermined points of time or at predetermined time intervals, a signal transmission device for receiving the sensor signals from the sensor device and for signal transmission of the sensor signals of the sensor device to an external reception and/or transmission device, a power supply device for supplying electric energy to the sensor device and to the signal transmission device, wherein the diagnostic system comprises a device for the determination of a second operational condition of the system component, and wherein the control function is realized such that at the predetermined points of time or at the predetermined time intervals it performs a detection of the second operational condition of the transmission mechanism and compares it to a predetermined comparative value and only provides the sensor value corresponding to the respective first operational condition to the signal transmission device if it is higher or lower than this comparative value.

The system component may in particular comprise a transmission mechanism having a housing. Moreover the sensor device may comprise a sensor for the determination of the water content of the lubricant contained in the container of the transmission mechanism.

In accordance with one embodiment of the invention, the device for the determination of a second operational condition of the system component may comprise a temperature sensor which measures the temperature in the housing and/or in the surroundings of the housing, and/or a pressure sensor which measures the pressure in the housing and/or in the surroundings of the housing.

According to a further embodiment of the diagnostic system of the invention, the transmission and reception module is realized such that it is adapted to be switched between a standby mode and a transmission mode, and that it comprises: an antenna device, a querying function for querying the signal strength present at the antenna device at predetermined points of time, a comparison function for determining that the detected signal strength present at the antenna device is higher than a predetermined limit value, and depending on this, generation of an activation signal to the transmission commanding function and a transmission commanding function for activating the antenna device for the reception and the transmission of signals between the signal transmission device and the external reception and/or transmission device, wherein the transmission and reception module is realized such that due to the activation of the transmission mode it generates signals for the sensor values detected by the sensor and transmits them to the antenna device for transmission to the external reception and/or transmission device.

According to a further embodiment it may be provided that the maximum transmitting power furnished by the signal transmission device is adjusted or may be adjusted by means of the control function of the signal processing device on the basis of a predetermined value or may be adjusted by means of the external reception and/or transmission device.

The maintenance device may in particular include a processing function for determining, on the basis of the sensor signal, a value for the operational condition of a lubricant present in the housing part. According to one practical example, the maintenance device is releasably or fixedly installed in the vehicle in which the lubricant container comprising the housing part is also integrated. Alternatively or additionally it may be provided that the maintenance device is a mobile maintenance device which may in particular be realized as a hand-held apparatus.

In the diagnostic system it may be provided that the sensor device includes a measurement function wherein at least one temporal specification for the performance of a measurement and a function of performing the measurement are set up, which measurement function activates the sensor when the temporal specification is satisfied and detects sensor signals for the determination of sensor values, that the maintenance device comprises an input device functionally communicated with the transceiver for querying a sensor value, which input device drives the transceiver of the closure device in response to an actuation of the input device, activates it for the transmission of a signal corresponding to the detected sensor signal, and receives this signal. In this practical example it may in particular be provided that measurement signals are generated with the aid of the timer through the measurement function and stored in the memory device. In response to the activation signal by the maintenance device, the measurement signal or a sensor value determined from the latter is transmitted via the transceiver to the maintenance device where it may be displayed.

It may furthermore may be provided that the sensor device is configured such that in response to receiving a control command from the transceiver associated to the sensor device, it detects a sensor signal corresponding to an operational condition of the lubricant and transmits it to the maintenance device.

According to one practical example of the diagnostic system of the invention it is provided that the sensor device includes: a processing function for determining a value for the operational condition of a lubricant present in the housing part on the basis of the detected sensor signal, and a diagnosis function functionally communicated with the processing function for determining maintenance information from the respective determined value for the operational condition of a lubricant present in the component housing part. In this way the maintenance function does not need to include any sensor-specific evaluation or diagnosis function. If the sensor is replaced, the maintenance device does not need to be adapted as in this case it does not include a specific evaluation and diagnosis function. Moreover, the evaluation or diagnosis function in the sensor device may be adapted to each single sensor, for instance in order to calibrate or match the sensor evaluation or the specific sensor. Alternatively, the diagnosis function may be integrated in the maintenance device.

The maintenance device may comprise a display device for displaying the sensor quantities and/or determined maintenance information. Moreover the maintenance device may be a hand-held maintenance apparatus in which the processing function and the display device are structural.

According to a further aspect of the invention, a diagnostic system having a maintenance device in accordance with one of the embodiments of the invention is provided, wherein the maintenance device includes a comparison function functionally communicated with a sensor device for supplying sensor signals which is realized in accordance with the invention and arranged in a component to be monitored, which is realized in such a way that the comparison function compares the respective detected measurement signal to two limit values and identifies, based on this comparison, whether the respective detected signal value is situated in a first range below a first limit value or in a second range between the first limit value and a second limit value greater than the first limit value, or in a third range above the second limit value. In this case the maintenance device includes a display function which carries out, based on the identification of a range for the respective detected signal value, marking of one of three fields each associated to one of the ranges in a display format of the display device. The comparison function may also be integrated in the sensor device, so that the sensor device determines the allocation of the signal value determined therein to the first, second or third range, which information is transmitted to the display device and displayed by the latter. In this embodiment the sensor device determines, following detection of the sensor value and with the aid of a mentioned comparison function, to what range the respective detected sensor value belongs. By way of example, the third range may designate a critical range, the affirmation of which is to indicate the necessity of replacing the component in which the sensor device is integrated. Here the first range may designate an admissible range, the affirmation of which is to indicate that the component is in an admissible operational condition and no maintenance measures are required. The second range may designate an admissible range, the affirmation of which is to indicate an operational condition of the component which, although admissible, forebodes a maintenance measure or requires a specific maintenance measure.

Alternatively it may be provided that only one limit value is predetermined, so that at least it may be displayed whether the limit value has been exceeded or has not been reached.

Allocation to the first and/or second range and displaying the presence of the first and/or second range may also be omitted, so that only the requirement of replacing the component is determined and optionally also displayed. In these cases the maintenance device of the invention may include a comparison function which is functionally communicated with the sensor device for supplying sensor signals and realized such that the comparison function compares the respective detected measurement signal to at least one limit value and identifies, based on this comparison, whether the respective detected signal value is situated in a first range below this limit value or in a second range above this limit value, and such that the maintenance device includes a display function which performs, on the basis of the identification of a range for the respective detected signal value, marking of at least one field or one of two fields each associated to one of the ranges in a display format of the display device. If only one range is provided in the display device and in the associated functionality, this range may in particular indicate a previously mentioned critical range. If two ranges are provided in the display device and in the associated functionality, one of these ranges may in particular indicate a previously mentioned critical range, and the other range an admissible range.

Moreover it may be provided that the maintenance device comprises a function module whereby a value for an operational condition of a lubricant present in the housing part may be selected, whereby a maintenance information necessary for a maintenance task may be transmitted to a display means and displayed by means of the display means. By way of example, the operational condition value may be the water or humidity content and/or the temperature in the component in question.

According to a further practical example of the diagnostic system of the invention it is provided that at least two sensor devices are integrated in the housing part, that the maintenance device includes a comparison function functionally communicated with the transceiver of the maintenance device, and a comparison function value which is used as a value for the operational condition of a lubricant present in the housing part is formed on the basis of the sensor signals from two different sensor devices. It may moreover be provided that the comparison function is realized in such a way that it uses the respective greatest signal value of the different sensor devices of a lubricant container as a determined signal value to be displayed. This practical example presents the advantage that the security of determination and display of the lubricant condition is enhanced. In this case not only local differences of the operational condition of the lubricant but also errors at the sensor device or at a component part of the closure device may be compensated.

There is furthermore the possibility of determining a consolidated value between the two determined sensor values, e.g. an average value, which is used for one of the comparison, evaluation and/or maintenance functions provided in accordance with the invention.

These functions may be preceded by a safety or error recognition function which compares the respective at least two sensor values determined by different sensor devices within a time period as to a deviation from each other and evaluates the sensor devices to be functional as long as the deviation of the two sensor values remains within predetermined boundaries. For such an error recognition function it is also possible to use more than two sensor devices, so that a sensor device having a sensor value is evaluated to be faulty and is not used any more when the sensor value of this sensor device deviates by a minimum amount from the sensor values of the second sensor devices within a predetermined time period.

The transceivers of the maintenance device and the transceiver associated to the closure device and in particular belonging to the closure device may be functionally communicated with each other in a cordless manner or via a cable connection.

According to one aspect of the invention, there is in particular provided a diagnosing method for detecting and transmitting a sensor value concerning an operational condition of a system component to an external reception and/or transmission device, including the steps of:
  generating sensor signals corresponding to a respective first operational condition of the system component,
  performing measurements by means of the sensor device at predetermined points of time or at predetermined time intervals,
  determining a second operational condition of the system component,
  at the predetermined points of time or at the predetermined time intervals, detecting the second operational condition of the transmission mechanism and comparing it to a predetermined comparative value, furnishing the sensor value corresponding to the respective first operational condition to the signal transmission device only if it is higher or lower than this comparative value.

According to one aspect of the invention, a diagnosing method for assisting the maintenance of a land, air, water or underwater vehicle is provided, including the steps of:
generating a sensor signal for detecting an operational condition of a lubricant contained in the housing part with the aid of a sensor device integrated in a closure device of the housing part, and transmitting the sensor signal corresponding to the operational condition to the maintenance device,
based on the sensor signal transmitted to the maintenance device, determining in the maintenance device a value for the operational condition of a lubricant present in the housing part on the basis of the sensor signal, wherein the water content of the lubricant is determined only if it is determined in the same measurement process or within a predetermined time period that the temperature of the lubricant is higher than a minimum temperature.

According to a further aspect of the invention, a diagnosing method for assisting the maintenance of a land, air, water or underwater vehicle is provided, including the steps of:
generating a sensor signal for detecting an operational condition of a lubricant contained in the housing part by means of a sensor device integrated in a closure device of the housing part, and transmitting the sensor signal corresponding to the operational condition to the maintenance device,
based on the sensor signal transmitted to the maintenance device, determining in the maintenance device a value for the operational condition of a lubricant present in the housing part on the basis of the sensor signal, wherein the operational condition and in particular the water content of the lubricant is determined only if it is determined in the same measurement process or within a predetermined time period that the temperature of the lubricant is higher than a minimum temperature.

Here it may be provided that the sensor device itself, and in particular in response to activation by the timer, detects a sensor signal corresponding to the operational condition of the lubricant, determines from this a sensor value corresponding to the operational condition of the lubricant, stores the sensor value in a memory, and transmits the sensor value to the maintenance device in response to a request command received from the maintenance device.

Alternatively or additionally it may be provided that the maintenance device sends to the sensor device a request command for transmission of a sensor value corresponding to the operational condition of the lubricant, determination of the sensor value by the sensor device, and transmission thereof to the maintenance device.

According to one practical example of the diagnosing method it may be provided that a maintenance function is integrated in the maintenance device which determines maintenance information from the value for the operational condition of a lubricant present in the housing part. It may moreover be provided that the maintenance device displays the determined maintenance information by means of a display device.

In particular it may be provided in the diagnosing method that in the process of determining the value for the operational condition of a lubricant present in the housing part based on a sensor signal, a value for the water content in the lubricant bath is determined on the basis of a signal value detected by the sensor device.

In accordance with the invention it may moreover be provided that at least two sensor means are employed in one examination location, the sensor signals of which are transmitted to the processing unit to be compared there, wherein as a result of the comparison a comparison function value is formed which is underlaid the further processing. It may moreover be provided that the central processing unit compares the signals received from a sensor assembly group to predetermined limit values for these signals and visualizes on a display whether the received signal is situated within predetermined limit values for the signal. The diagnosing method may be configured in such a way that when a received signal is situated outside the range of the predetermined limit values, the processing unit outputs a warning signal, in particular an acoustic or visual warning signal. If the diagnosing method or the diagnostic system is configured such that the central processing unit receives signals from several sensor assembly groups, it may be provided that the relative position of the sensor assembly groups among each other and/or relative to the vehicle body of a land, air, water or underwater vehicle in which the sensor assembly groups are installed is displayed on the display device.

In the diagnosing method it may moreover be provided in particular that the maintenance device forms, based on the sensor signals of two different sensor devices each integrated in the housing part, a comparison function value which is used as a value for the operational condition of a lubricant present in the housing part, wherein in particular the respective largest one of the measurement values determined within a measurement period is used as a comparison function value.

In the diagnosing method the transmission of a command signal from the maintenance device to the transceiver integrated in the housing part and the transmission of the sensor signal from the transceiver to the maintenance device may take place in a cordless manner.

According to a further practical example it is provided that a satellite position sensor is integrated in the sensor device, or one respective satellite position sensor in each sensor device if several sensor devices or closure devices are used in one lubricant container, whereby the position of the closure device is determined. Here it may moreover be provided that this position is stored in the sensor device and in particular in a memory device thereof, and is transmitted to the maintenance device upon a query, optionally together with a respective sensor value.

In the diagnosing method of the invention it may be provided that sensor signals are generated and/or stored in at least one sensor device on high-maintenance partial systems or components of the vehicle in an examination location, the sensor signals being transmitted to the maintenance device which determines an operational condition on the basis of the sensor signals of different partial systems.

According to a further aspect of the invention, a land, air, water or underwater vehicle is provided in which a housing part of the invention and/or a diagnostic system of the invention is installed.

BRIEF DESCRIPTION OF THE DRAWINGS

The advantages and features of the present invention also become evident from the following practical examples in conjunction with the drawings, wherein:

FIG. 4 is a schematic representation of the end portion implemented as a capacitor and comprising a planar capacitor of the capacitor represented in FIG. 3a;

DETAILED DESCRIPTION

The closure device of the invention, the housing part of the invention, the diagnostic system of the invention, and the diagnosing method of the invention shall be explained in the following, in particular also on the example of an aircraft, and then in particular on the set of problems involved in determining the concentration of water inclusions in a lubricant reservoir.

According to one aspect of the invention, a closure device 20 for sealing an opening of a housing part 10 from a lubricant is provided which is realized as a screw or bolt and has integrated therein (FIG. 1): a sensor device for generating sensor signals corresponding to the operational condition of the lubricant, as well as a transceiver for the signal transmission of the sensor signals to an external reception unit, with a surface of the closure device 20 being realized as a sensor surface for the detection of the sensor values.

According to a further aspect of the invention, a housing part of a lubricant container is provided with such a closure device for sealing or for closing an inlet or outlet opening of the lubricant container. The housing part may generally be part of a lubricant container or entirely constitute the latter. The lubricant container comprising the housing part 10 of the invention may generally be intended for serving a reservoir or storage function. Alternatively or additionally, the lubricant container comprising the housing part 10 of the invention may be configured for receiving a power transmission mechanism 11 using a lubricant in operation, and at the same time as a lubricant container for receiving the lubricant required for lubrication of the power transmission mechanism 11.

Figure 1:
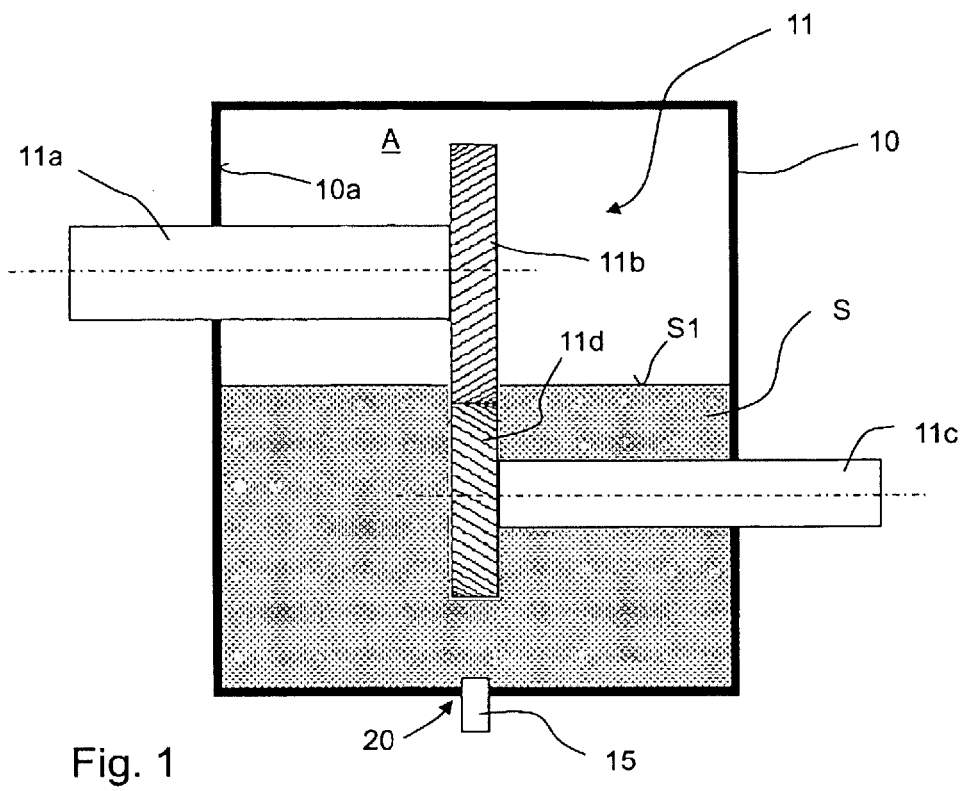
FIG. 1 is a schematic sectional representation of a power transmission mechanism having the form of a transmission, or gearing, which is accommodated in a housing part having the form of a lubricant container, wherein the housing part includes, in accordance with the invention, an outlet opening closed by a closure member.

In FIG. 1 a housing part 10 of the invention having a power transmission mechanism 11 arranged therein is represented schematically. This sectional representation shows the power transmission mechanism 11 accommodated in the housing part to have the form of a transmission comprising an input shaft 11a, a transmission wheel 11b arranged thereon and having the form of a gearwheel, an output shaft 11c, and a second transmission wheel or driven gear 11b arranged thereon and having the form of a gearwheel. Inside the housing part 10, which is formed integrally in the representation of FIG. 1, a lubricant S or a lubricating fluid for lubrication of the transmission mechanism 11 is present which is particularly in the liquid state in operational use.

In accordance with the invention, the housing part 10 has at least one inlet opening and/or at least one outlet opening for filling the lubricant S into the lubricant container or for draining the lubricant therefrom, each of which is sealed by a releasable closure device 20. The housing part 10 represented in FIG. 1 has an outlet opening 15 for draining the lubricant S in which the closure device 20 is inserted, so that after removal of the closure device 20 from the outlet opening 15, the latter is open and lubricant may escape through it from the housing part 10.

Here it may be provided that for the intended operation of the housing, or of the housing part, the lubricant does not entirely fill the housing or the housing part 10, resulting in the formation of a surface level S1 of the lubricant S in the housing or housing part 10. In this case, an opening of the housing part 20 of the invention in which a closure device of the invention comprising a sensor device is inserted is situated in a range below the surface level S1 of the lubricant S of the housing comprising the housing part 10 of the invention when the housing or the housing part 10 is assembled or installed in its intended location, so that during operation of the housing or of the housing part 10, the opening or the sensor device is situated in or at a lubricant-filled area in the normal condition. Hereby it is ensured that the operational condition of the lubricant may be detected in the normal condition.

In the application in which the housing is filled only partly with lubricant for the operational condition of the housing comprising the housing part 10 of the invention, the opening having a closure device of the invention inserted therein may in particular be a lubricant outlet opening that is situated, at an intended orientation of the housing, below the surface level S1 of the lubricant S present in the housing for the operation.

In a specialized exemplary application of the invention in which the housing part is a part of a housing or the housing for a power transmission mechanism 11 and in particular a rotary actuator for adjusting an aerodynamic flap of an aircraft (FIG. 2), it may in particular be provided that the housing comprising the housing part of the invention is filled with lubricant to no more than between 40% and 80% of the housing capacity.

The installation of the housing comprising the housing part of the invention and the position of the opening on the housing are provided such that the opening with the closure device of the invention is situated below the surface level S1 of the lubricant S present in the housing for the operation.

Figure 2:
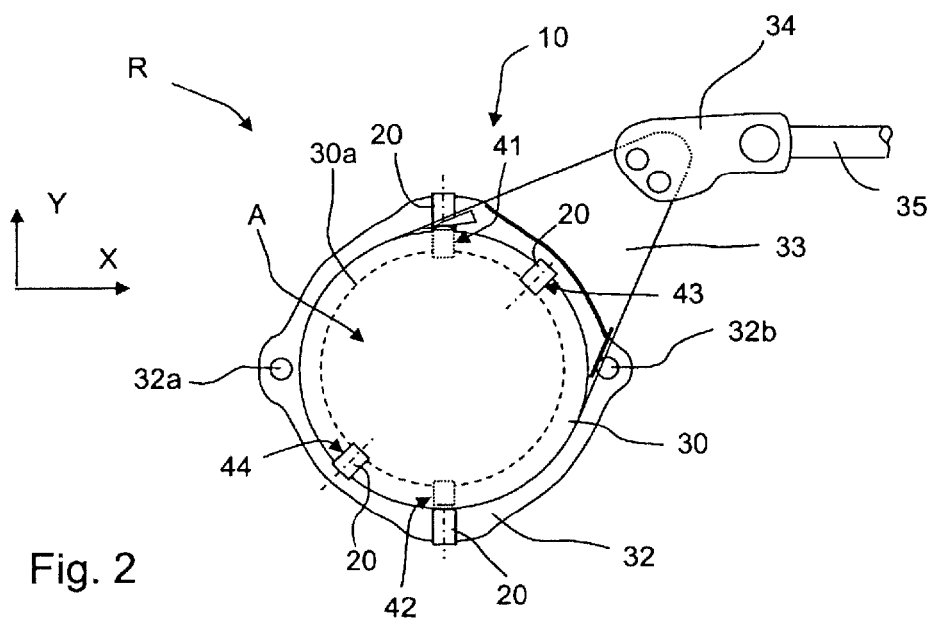
FIG. 2 is a schematic top view of a practical example of a rotary actuator generally as a transmission mechanism comprising a base plate and a housing part having the form of a lubricant container, wherein a power transmission mechanism implemented as a transmission is received.

The practical example of a housing 10 of the invention represented in FIG. 2 is intended for receiving a rotary actuator R as a power transmission mechanism 11 and is made up of a rotatable housing part 30 and a second housing part realized as a base body 32 or flange body, wherein the housing part 30 is rotatably arranged on the base body 32. The base body 32 is intended for fastening to a structural component and has two flange bores 32a, 32b for this purpose. The rotatable housing part 30 forms on its inner side 30a an internal space A that is partly delimited by the inner side of the base body 32 facing this internal space. In FIG. 2 the inner wall 30a of the rotatable housing part 30 is represented as a dashed line. In the internal space A a transmission mechanism 11 (not represented) is installed, whereby an input power transmitted by an input shaft to the transmission mechanism 11 is transmitted by the transmission mechanism 11 to an output shaft (not represented). The transmission mechanism 11 may have the form of a transmission, and in particular a gearwheel transmission. The output shaft is coupled to an adjusting lever 33 that is coupled via a coupling device 34 to a transmission rod.

The represented rotary actuator R may in particular be used for adjusting an aerodynamic flap of an aircraft. The aerodynamic flap may in particular be a trailing edge flap of a main wing of the aircraft. In this application the base body 32 is fastened to a structural component of the main wing, and the transmission rod is coupled to the aerodynamic flap or the trailing edge flap, respectively. The rotary actuators R may generally be a transmission or a transmission device.

The rotary actuator R, or generally the component in question, may in particular be part of an overall system such as an actuation system or high lift system of an aircraft. The overall system may in particular be realized as an error-tolerant system while having a self-monitoring function whereby the integrity of the overall system is monitored and errors of components may be recognized. The overall system may include a reconfiguring function whereby components are not used any more if errors of these components are recognized. In accordance with the invention, the solutions of the invention including the sensor device and the maintenance or display functions are preferably realized as accessory device and accessory function, so that these have no influence on the complexity of the overall system and independently thereof provide a specialized monitoring function in accordance with the invention.

The housing part 10 of the invention may in particular be a housing part that is movable or rotatable relative to another housing part, with a dynamic seal being arranged between the housing parts. In the present context a "dynamic seal" is understood to be a seal which is arranged between parts that are movable relative to each other and, although sealing the internal space formed by those parts with respect to a lubricating fluid present in this internal space, nevertheless does not completely seal the internal space with respect to air. The housing part 10 of the invention may also be a housing part 10 having a recess through which protrudes a rotating part such as, e.g., an input shaft or generally a part that is movable relative to the housing part, wherein a dynamic seal is arranged between the part moving relative to the housing part and the housing part 10. In this case the housing part also comprises a reception for mounting a dynamic seal.

The housing part 10 of the invention may, but need not exclusively, have the form of a lubricant container and need not exclusively be provided for the purpose of lubricant reception. As may be seen in FIG. 1, the housing part 10 may also have the function of a cover as well as, for instance, the function of an adjusting element which is realized in the practical example according to FIG. 1 as an adjusting lever 33. The housing part 10, however, is part of a housing or the housing in which lubricant is present for the intended operation.

In the case of the represented rotary actuator R as an embodiment of a transmission mechanism for adjusting an aerodynamic flap of an aircraft (FIG. 2) it is in particular provided that the housing comprising the housing part of the invention is filled with lubricant only to a maximum of 80% of the housing capacity. The orientation of the base body 32 represented in FIG. 2 is the orientation in which it is installed in a structural component of an aircraft or fastened thereto. In FIG. 2 an XY-coordinate system is specified in which the Y-direction indicates the direction of gravity. The housing part 30 is shown in a position in which the transmission element 35 holds the flap coupled to it in an extended state. The housing part 30 is thus rotated counter-clockwise when seen in the viewing direction of a person viewing FIG. 2 when the rotary actuator R takes the transmission element 35 to a retracted position.

The practical example of the rotary actuator R represented in FIG. 2 has in the base body 32 an inlet opening 41 for introducing lubricant and an outlet opening 42 for draining the lubricant. The housing part 30 of the rotary actuator R according to FIG. 2 moreover also has an inlet opening 43 for introducing lubricant and an outlet opening 44 for draining the lubricant. According to an alternative practical example it is also possible that only one inlet opening and only one outlet opening are provided on the rotary actuator R according to FIG. 2, wherein in this case the inlet opening and the outlet opening may each be disposed on the base body 32 and/or on the rotatable housing part 30.

As the installation of the housing comprising the housing part of the invention and the position of the opening having a closure device according to the invention is provided on the housing such that the opening having the closure device of the invention is situated below the surface level S1 of the lubricant S present in the housing for the operation, in the represented practical example the outlet openings 45, 44 are each provided with a closure device according to the invention. Alternatively it is also possible that only one of the outlet openings, i.e. the outlet opening on the base body 32 or the outlet opening on the rotatable housing part 30, is provided with the closure device of the invention. In each of the further openings a closure device without a sensor device may be inserted for closing it.

FIGS. 3a, 3b, 5 and 6 represent embodiments of the closure device 20 of the invention comprising a housing 30a which generally has a first end portion or first end portion 31 having a first outer surface or end surface 31a, a second portion or end portion 32 situated opposite therefrom relative to the longitudinal direction of the closure device 30 and having a second end surface 32a, and a longitudinal side 33 or outer side extending along the longitudinal direction L. When the closure device 30 is installed in the housing part 10 in accordance with its intended purpose, the first portion 31 faces the internal space of the housing part 10, so that in the event of a corresponding operational use of the housing part 10 the lubricant present therein may enter into contact with the first portion 31 of the housing part 10.

Figure 3A:
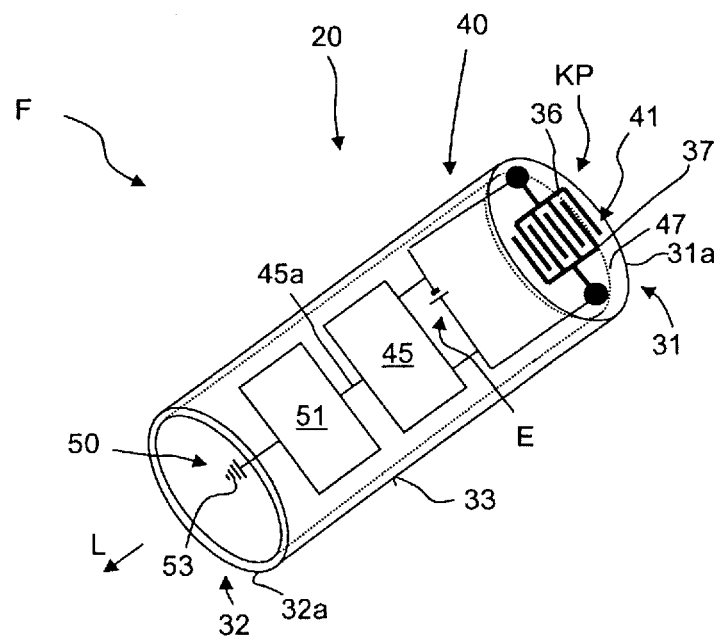
FIG. 3a is a schematic representation of a practical example of a closure member provided in accordance with the invention and having an end portion realized as a capacitor, in which a sensor device and a transceiver as well as a power supply for the capacitor are functionally integrated, and wherein the capacitor is implemented as a planar capacitor.

In accordance with one embodiment of the invention, the housing part 10 and/or the closure device 20 comprises a function module F or generally a diagnostic system which comprises: a power supply device E which may in particular be implemented to be self-sufficient with a battery and/or a power generator, a sensor device 40 comprising at least one sensor 41 generally for the determination of the operational condition of the lubricant and a signal processing device 45, and a signal transmission device 51 functionally communicated with the signal processing device 45 via a connection line 45a (FIG. 3a).

In accordance with the invention, the function module F is generally installed in a housing or housing part of a transmission mechanism such that the first portion 31 faces the internal space of the housing part 10. The function module F may be integrated in a separate housing 30a. Alternatively the function module F itself may be integrated in a recess or an internal space provided by the housing part of the transmission mechanism or in an inner wall of the latter. The function module F is in particular realized in such a way that there is no electrical connection from it to the vehicle or aircraft having the housing part of the invention or the container of the invention integrated therein due to the power supply device E or the functions of the signal transmission device 52 for wireless communication and transmission of information and/or sensor data.

Figure 3B:
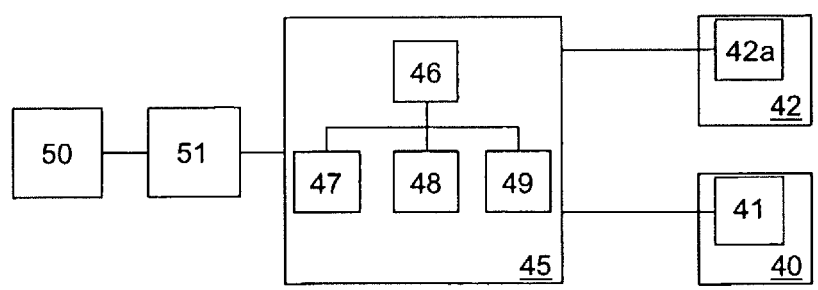
FIG. 3b is a functional representation of an embodiment of the function module of the invention comprising the sensor device and a transceiver, for installation generally in a transmission mechanism.

Moreover the function module F may comprise a device 42 for the determination of the operational condition of the lubricant container or of the transmission mechanism (FIG. 3b). This device 42 may be constituted by one or several further sensors, namely, in particular a pressure sensor for detecting the pressure in the inner and/or outer space of the container and/or a temperature measuring device 42a for detecting the temperature in the internal space of the container and in particular the temperature of the internal space of the container and in particular of the lubricant in the container. Alternatively or additionally the device 42 may comprise a sensor for detecting a transmission force occurring in the transmission mechanism and, for example, a strain sensor such as a strain gauge or an arrangement of strain gauges. The device 42 for the determination of the operational condition of the transmission mechanism may also be constituted by a movement or vibration sensor and an associated sensor evaluation capable of detecting whether the transmission mechanism is in operation or whether the transmission mechanism had not been moving and thus not operating since a minimum time interval.

Furthermore, if the solution of the invention is applied in an aircraft, the device 42 may be or comprise an interface with an aircraft system furnishing the information that the aircraft or the transmission mechanism is not in operation or that the environmental pressure and/or the environmental temperature is situated above a respective minimum value. The device 42 may also be made up of a combination of the aforementioned alternatives.

The signal processing device 45 is functionally communicated with the sensor device 40 and the device 42. The signal processing device 45 may in particular comprise a control device 46 which may be functionally communicated with a memory device 47, optionally with an evaluation function 48 and optionally with a timer 49 (FIG. 3b). The control device 46 may in particular include a function whereby in cooperation with the timer 49 a measurement by means of the sensor device 40 and in a given case by means of the device 42 is performed at predetermined points of time or at predetermined time intervals. Storing the detected sensor values in the memory device 47 is moreover carried out by means of the control device 46. Moreover an evaluation function 48 may be provided whereby sensor values detected by the sensor device 40 and in a given case by the device 42 may be stored in a predetermined manner. For example, it may be provided with the aid of the control device 46 and the memory device 47 that up to a maximum number all of the measurement values of the named and respective active sensors are optionally stored with a respective time value or an indication of time. Alternatively it may be provided that precisely the respective most recent measurement value is in a given case stored together with a time value. The evaluation function my include a functionality whereby the detected sensor values are processed. Here it may be provided, for instance, that respective average values are formed on the basis of a predetermined number of detected sensor values and one respective average value or several average values from different series of sensor values are transmitted to the external reception and/or transmission device.

Moreover a safety function may be integrated in or with the evaluation function which determines, e.g. by way of a plausibility examination, whether the detected sensor values include an error. In particular the safety function may be implemented such that it associates an error state to a sensor, e.g. to the sensor 41, the sensor device 40 and/or the function module F if the latter furnishes sensor values deviating in one iteration or in several iterations by a minimum amount from an average value of sensor values or from the average value of the sensor values generated by the respective sensor. Alternatively or additionally the function module F may be realized in such a way that a sensor such as, e.g., sensor 41 is realized as multiples, i.e. redundantly, and the safety function is realized in such a way that it associates to a sensor, e.g. sensor 41, sensor device 40 and/or the function module F if the values of respective redundant sensors deviate from each other in one iteration or in several iterations by a minimum amount. The safety function furthermore preferably includes a function whereby a determined error state is transmitted by means of the control device 46 via the transmission and reception module 51 upon a respective inquiry to the external reception and/or transmission device so as to indicate that the detected sensor values are erroneous and not usable. One consequence from this may be that a maintenance measure for examining the transmission mechanism and in particular the function module F has to be carried out.

The control function 46 may further include a self-test function for testing the function module F. In this case the control device 46 may be realized in such a way as to store the result of the self-test used in particular in order to determine whether the function module is ready for use and/or functional, in the memory device and/or transmits it to the external reception and/or transmission device upon a corresponding inquiry.

The signal processing device 45 of the sensor device 40 may include a measurement function for the performance of the measurement and generation of a measurement value corresponding to the respective measurement signal detected by the sensor 41 or the further sensor, which measurement function is functionally communicated with the at least one sensor 41 and—if a further sensor for detecting an operational condition of the transmission mechanism exists—with such a second sensor and a measurement value memory or a memory device functionally communicated with the measurement function. The measurement function may in turn be communicated with a timer. In this case a time value such as, e.g., a time which was detected together with the measurement value resulting from a measurement of the at least one sensor 41 is output or stored in a measurement memory together with the measurement. The timer may in particular be a real-time clock. Here the function module F may furthermore be realized such that the measurement value is stored together with a time value in the memory device, and the measurement value together with the respective time value is provided by the commanding function for transmission by the antenna device 52.

Moreover the signal processing device 45 and in particular the measurement function thereof may also include a function for detecting the power condition of the power supply device E or for detecting the supply voltage of the at least one sensor 41. Here it may be provided that the status of the supply voltage is queried in response to a query directed to the control device thereof by an external reception and/or transmission device via the signal transmission device 52 in the framework of the function for detecting the power condition and is transmitted to the external reception and/or transmission device in the described manner, in accordance with the invention, as information concerning the operational condition of the functional group. In this way it may further be provided that further information concerning the operational condition of the functional group, such as status information concerning functions thereof, is transmitted to the external reception and/or transmission device. In accordance with one embodiment of the functional group of the closure device 20, it may alternatively or additionally be provided that these data as well as sensor data generated in accordance with the invention by the sensor device 40 may be retrieved by directly coupling an external reception and/or transmission device via a connecting cable or via a user interface.

The control function may, for example, be a partial function of the sensor device 40 or an autonomous function module in addition to the sensor device 40.

In one practical example the sensor 41 of the sensor device 40 comprises at least one capacitor K. The further sensor may, e.g., be at least one air pressure sensor for detecting the altitude and/or at least one temperature sensor.

In accordance with one practical example of the invention it may be provided that the measurement function for repeated performance of measurements takes place at predetermined time intervals, so that the at least one sensor 41 generates sensor signals at predetermined time intervals and thus in a quasi-continuous manner. To this end, the control device drives the at least one sensor 41 at predetermined time intervals and initiates a measurement of an operational condition of the lubricant.

Particularly in these embodiments the sensor device 40 may be realized in such a way as to perform the measurement by means of the sensor 41 only if it is determined by means of the sensor device 40 that the further sensor determines a trigger information or a minimum value for an operational condition of the transmission mechanism and, depending on its implementation, in particular a minimum temperature of the environment or of the lubricant. In this embodiment of the invention the control function of the signal processing device 45 causes the performance of a measurement of the operational condition of the lubricant by means of the sensor 41 and storing of this measurement value, optionally together with an associated time value. In accordance with one embodiment it is provided that the measurement function initially determines the temperature of the lubricant by means of the temperature sensor and performs a measurement of the operational condition and in particular of the water content in the lubricant only if the temperature is situated in a predetermined temperature range. For the application of the invention in an aircraft it is in particular possible to fix the temperature range between −20 degrees and 60 degrees Celsius at which the measurement takes place. With use in an aircraft it may be expected as a certainty below and/or above this temperature range, i.e. in this example in particular below −20 degrees, that at this time a query of measurement values by means of an external reception and/or transmission device does not take place, i.e., that the querying function does not determine a signal strength at the antenna device 52 corresponding to a query.

In an alternative embodiment the control function is realized in such a way that it allows to detect the measurement of the operational condition of the lubricant and of the further operational condition by means of the further sensor at predetermined time intervals, however carries out storing of the respective detected measurement values only if the further sensor determines a trigger information or a minimum value for an operational condition of the transmission mechanism. The minimum value for an operational condition of the transmission mechanism may be—depending on the embodiment of the function module F in particular comprising a temperature sensor or a pressure sensor—a minimum temperature or a minimum pressure of the environment or of the lubricant. Alternatively or additionally the operational condition of the transmission mechanism may be an extensometer for determining a strain on a transmission element of the transmission mechanism, and thus a tension or a force in this location. The further sensor may in this way and in a given case determine with the aid of the timer whether and for how long the transmission mechanism has remained inactive and thus how for how long it may be considered to have been out of operation. To this end, the signal processing device 45 may include an evaluation function wherein the comparison between the minimum value for an operational condition of the transmission mechanism and the actual value for the operational condition is carried out and it is determined whether the actual operational condition is below the minimum value, and thus for how long the transmission mechanism has not been in normal operation, and thus for how long it may be considered to have not been in operation or out of operation. In accordance with one embodiment of the invention it is assumed for this time period that within this time period there is a likelihood of a query by an external reception and/or transmission device, which may be detected by a signal strength present at the antenna device 52. The function module may be implemented such that during this time period no measurement of the operational condition of the lubricant in particular by means of the sensor 41 takes place, in order to thereby reduce the energy consumption of the function module F, and at time intervals carries out a measurement of the operational condition of the lubricant if it is assumed apart from this that the transmission mechanism is not in the normal use or operational condition.

In one embodiment of the invention, the time interval between two respective measurements of the operational condition of the lubricant and in a given case of the further operational condition is relatively great, and preferably amounts to one or several days. The control function may moreover be realized such that the measurement is carried out at shorter intervals, e.g. once every hour, if it is thereby established that the transmission mechanism is not in normal use or operational condition. In one further development of this embodiment of the invention it may be provided that in case it is found at a predetermined number of measurements of the further operational condition and e.g. at 10 measurements that the lubricant is outside a predetermined range while being in normal use or operational condition, no further measurement takes place over a substantially greater time period and e.g. over one week or in a time period between one day and one month, and only after this time period a measurement of the operational condition of the lubricant is carried out again.

The signal transmission device 50 may in particular be constituted by a transceiver 51 or a receiver/transmitter or generally a transmission and reception module as well as an antenna device 52 connected to the latter and comprising an antenna and optionally an antenna amplifier for the transmission of output signals having been generated by the signal processing device 45, to an external reception and/or transmission device such as, e.g., a maintenance device which may in particular be realized in accordance with the invention, and for receiving control signals from an external reception and/or transmission device such as, e.g., a maintenance device. In accordance with the invention, the transmission between such an external reception and/or transmission device and the signal transmission device 50 preferably takes place by wireless, however may also take place via a cable connection.

Moreover it may be provided that the maximum transmitting power furnished by the signal transmission device 52 is set or, e.g., is adjusted by means of the control function 46 of the signal processing device 45. Here the transmitting power is set within a range that is admissible for the operation of the transmission mechanism in a range of use. Hereby it is ensured that transmission processes likely to interfere with other systems, e.g. on an aircraft in flight, will be carried out. Moreover there is a high probability of avoiding a failure involving transmitting at a high transmitting power. Moreover in this embodiment a transmission mode is possible in a service event and in particular in a maintenance measure only.

The transmission and reception module 51 may be realized such that it brings the sensor values to be transmitted into a transmission format and can transmit in the latter to the external reception and/or transmission device. In accordance with one embodiment in accordance with the invention, the transmission and reception module 51 is realized such that it reads in the signals received from the antenna device 53 and transforms them into data and information as well as transmits them to the signal processing device 45 for further processing, or are furnished for being read in by the signal processing device 45. Moreover the transmission and reception module 51 may be realized such that it reads in data and information furnished by the signal processing device 45 or retrieves them from the latter. Moreover the signal processing device 45 may in particular be realized such that it transmits obtained or determined data or information to the transmission and reception module 51 as soon as they are present in the signal processing device 45. In these cases the respective transmission or the respective retrieval of data or information preferably takes place at predetermined iteration rates at which the signal processing device 45 and the transmission and reception module 51 communicate with each other.

In accordance with one embodiment of the invention, the transmission and reception module 51 has a transmission function including a querying function, including a comparison function and a transmission commanding function for activating the antenna device 53 for the reception and the transmission of signals between the signal transmission device 50 and the external reception and/or transmission device. The querying function is realized such as to query at predetermined time intervals the signal strength present at the antenna device 53 and detect the respective signal strength present. The comparison function receives the respective signal strength present at the antenna device 53 and compares it to a limit value in order to determine whether a query or a communication attempt from the external reception and/or transmission device exists. If the respective detected signal value reaches or exceeds this limit value, the comparison function values this as the presence of a query by an external reception and/or transmission device and provides the transmission commanding function with corresponding information in this regard. Thereupon the transmission commanding function generates a command signal for activating the transmission and reception module 51 for a transmission of signals to the external reception and/or transmission device. The antenna device 53 is implemented such that upon reception of such a command signal from the transmission and reception module 51 it adjusts the signal strength for receiving and/or sending signals. Moreover the transmission and reception module 51 generates signals whereby the sensor values detected by the sensor 41 are transmitted to the antenna device 53. To this end, the transmission and reception module 51 reads in at least one sensor value detected by the sensor 41 from the signal processing device 45, which is furnished by the signal processing device 45. The signal processing device 45 may comprise a memory device in which at least one sensor value from the sensor 41 is stored.

The querying function may be set up such that the query takes place through a detection of the signal value present at the antenna device 52 at predetermined and particularly regular intervals. Here it may be provided that the time intervals are provided to be relatively short, i.e. they are provided at an interval corresponding to an expected response time for a query by the external reception and/or transmission device and in particular a user of the external reception and/or transmission device. The time period between the queries may be between 0.1 sec and 5 sec. Alternatively or additionally it may be provided that the transmission and reception module 51 includes a storage function whereby the presence of a signal strength corresponding to query is stored, and the time period between the queries is as described above or even substantially greater than the aforementioned time period and is, e.g., on the order of minutes or hours, i.e. in particular between 1 and 60 min or between one hour and 36 hours.

According to one further development in accordance with the invention of this functionality, the antenna device 52 is realized such that it may assume two operating modes, a standby mode and a transmission mode for transmitting and receiving signals or data, wherein maintaining the standby mode requires substantially less and in particular up to 80% less energy than the transmission mode in which higher energy and power (power at least 50% greater than in the standby mode) is furnished by the energy supply E to enable transmission of signals to an external reception and/or transmission device. Switching between the operating modes may here be executed by the commanding function of the transmission and reception module 51 for activating the antenna device 52 and/or by the control device and generally by the . . . ???. The commanding function preferably is realized such that it receives or retrieves from the querying function a corresponding information that, or whether, a query by an external reception and/or transmission device exists based on the determination of the signal strength present at the antenna device 52. In this case the commanding function for activating the antenna device 52 reads in data of the sensor device 40 and in particular of the sensor 41 provided in the memory device, generates a command signal for activating the antenna device 52 for the reception and the transmission of signals between the signal transmission device 50 and the external reception and/or transmission device in order to switch the antenna device 52 from the standby mode to the transmission mode, and transmits this one command signal to the antenna device 52, so that the latter then switches from the standby mode to the transmission mode. Moreover the commanding function sends the sensor data provided by the sensor device 40 in a predetermined transmission format to the antenna device 52. Alternatively or additionally the commanding function may also be integrated in the control function if the latter receives the signal values or the result of the comparison from the querying function.

In accordance with one embodiment of the invention in which the measurement function carries out a repeated performance of measurements at predetermined time intervals, these time intervals may in particular be different from the time intervals at which the presence of a query at the antenna device 52 or the transmission and reception module 51 by an external reception and/or transmission device is determined.

In accordance with one practical example of the invention it may be provided that the measurement function for the repeated performance of measurements takes place at predetermined time intervals, so that the at least one sensor 41 generates sensor signals at predetermined time intervals and thus in a quasi-continuous manner. To this end, the control device drives the at least one sensor 41 at predetermined time intervals and initiates a measurement of an operational condition of the lubricant.

The function module may also be realized such that the sensor data is taken directly from a current detection step owing to a function of the commanding function of the sensor device.

Alternatively the commanding function may also be part of the signal processing device.

By this functionality it is achieved that during the period in which the transmission of data and information is not to be performed due to the absence of a query, the antenna device may be set to a low signal strength corresponding to the standby mode, at which at least one query may be detected by an external reception and/or transmission device by means of the querying function. In this way the function module may be operated in an energy-efficient manner. The transmission mechanism may be operated by means of a battery as a power supply E over a multiplicity of operating cycles, so that a maintenance measure with regard to the lubricant present in the transmission mechanism is required and to be carried out only when the sensor device 40 has detected a critical operational condition of the lubricant.

Alternatively or additionally it may be provided that the respective detected sensor value may be read out directly at the sensor device or at the control device, such as, e.g., via a cable connection and signal line coupled thereto or a user interface.

Alternatively or additionally, the initiation of an energy-saving standby mode and an active transmission mode of the sensor device 40 may moreover be carried out by the external reception and/or transmission device such as, e.g., a maintenance device, if the latter as well as the signal transmission device 52 and in a given case associated functions are realized accordingly.

In a further embodiment the signal transmission device 52 may be realized such that in the energy-saving standby state it may receive queries by an external reception and/or transmission device such as, e.g., a maintenance device.

According to a further embodiment of the housing part of the invention or of the function module F it is realized such that the sensor device 40 in particular stores: maintenance measures performed on it such as, in particular, the point of time of initial operation of the functional group or a function thereof such as the control device, points of time of maintenance measures, the point of time of a battery change, and/or the exchange of lubricant. This information may be transmitted to the function module F, for example with the aid of the external reception and/or transmission device and in particular a maintenance device, so that these values are stored, e.g., in a maintenance module of the function module F and may be kept available for an inquiry from an external reception and/or transmission device.

In accordance with one further development, the function module F and in particular the control device may include a self-test which performs a self-test of the function module F and stores the result information concerning this self-test in particular in the memory device, wherein the function module F is realized such that this information may especially be transmitted in the described manner to an external reception and/or transmission device. The latter may be set up such that the transmission of the self-test information takes place separately upon inquiry or jointly with a query of the sensor values.

In one embodiment in accordance with the invention it is possible that the query is registered, e.g., by the transmission and reception module 51 as a query concerning the sending of a measurement value or information of the lubricant, only if an address specified by the query is identical with a predetermined address.

Here it may be provided in particular that this information may be transmitted to the external reception and/or transmission device via a connecting cable or via a user interface in one or several ones of the described manners.

Moreover the driving device may be realized such that the performance of measurements of the water content in the lubricant is initiated at predetermined time intervals and the sensor device switches to a standby state between the measurements, and that it switches the antenna device to an energy-saving standby state while examining on the transceiver whether a query made by a maintenance device concerning the operational condition of the lubricant has arrived, and that in the presence of a query by an external reception and/or transmission device such as, e.g., a maintenance device, the control device switches the signal transmission device 52 from a standby state to a transmission mode and initiates the signal transmission device 52 or the transceiver to transmit a sensor value concerning the operational condition of the lubricant.

According to another embodiment of the invention, the sensor measures at predetermined time intervals, then enters into the standby state, at each measurement writes the measurement signal values into a memory, e.g. a flash memory or an EEPROM.

According to this embodiment, sending the sensor data determined by the sensor device to the external reception and/or transmission device thus takes place by way of querying the latter. Here it may particularly be provided that the respective current sensor value, i.e., the respective most recent value is output to the signal transmission device 52, a connection device, or a user interface.

According to a further embodiment of the functional group, the latter may be realized such that for the case of the signal transmission device 52, a connection device or a user interface receiving a query or information request, the control device initiates a transmission operation via the corresponding interface.

The external reception and/or transmission device may be realized as a PC or PDA comprising a wireless module. Here it may in particular be provided that the external reception and/or transmission device addresses the sensor device via an address to command in this manner the sensor device to perform functions such as, in particular, setting parameters of the sensor device 40, carry out measurements by means of the at least one sensor 41, and/or read out data from a memory of the sensor device 40 and transfer it to the external reception and/or transmission device. The external reception and/or transmission device may be realized such that it may analyze received measurement data. Moreover the external reception and/or transmission device may include functions whereby it is determined on the basis of the determined operational condition of the lubricant whether the lubricant still is in a condition fit for operation or has to be exchanged. The sensor device 40 and/or the external reception and/or transmission device may be realized to store a service query and/or the result of the response to the query and furnish it via an external reception and/or transmission device via a connecting cable or via a user interface upon a corresponding query. Moreover the functional group may be realized such that the adjustment of system parameters and in particular of functional parameters of the functional group may be carried out in the course of maintenance measures. Moreover the functional group may be realized such that a test measurement may be carried out in response to a query by means of the sensor device 40. According to a further embodiment of the functional group, it may include a satellite positioning system such as a GPS receiver integrated into the functional group in such a way that in response to a corresponding query by an external reception and/or transmission device via a connecting cable or via a user interface, respective information concerning the position of the functional group or of the housing part is provided. In this way a detection of the position of the functional group or of the housing part on the vehicle or aircraft is possible. This is advantageous in particular if several functional groups or housing parts of the invention are present on the vehicle or aircraft, so that information transmitted by the functional group allows an identification in which position the functional group having sent data is installed. Moreover this function also allows to determine the position of the vehicle or aircraft on the ground, in the takeoff phase, the cruising phase or landing phase, in particular a temperature profile and/or pressure profile over time or in the in-flight phase and/or the position of the aircraft or single temperature and/or pressure values in single positions and transmit them in the described manner.

According to a further embodiment of the invention, the signal transmission device 52 may furthermore be realized such that particularly by initiating a control function thereof, it may switch the sensor device 40 to an energy-saving standby state or an active measurement mode in which the signal values and—depending on the embodiment—in a given case further detected information concerning the operational condition of the container may be transmitted. The standby state or sleep state is an energy-saving mode in which the sensor device 40 has only a low or minimum power demand but may nevertheless be addressed functionally, particularly by the control function and/or the transmission and reception module 51 and/or the external reception and/or transmission device. In the active measurement mode higher power is supplied by the power supply device E, which is necessary for the activation of measurement functions and the performance of measurements.

According to a further embodiment, the control device may be realized such that it causes the signal transmission device 52 to have no transmission activity and in particular wireless transmission activity if the temperature detected by the sensor device 40 is below a predetermined value and, e.g., below 20 degrees C. This presents the advantage that energy may be saved, for at a temperature below the minimum temperature there is a high likelihood of the aircraft being airborne and no service or maintenance measure being required.

According to one practical example, the closure device of the invention 20 may be realized as a screw and for insertion in particular along the longitudinal direction of the closure device 30 in a threaded reception of an opening, i.e. the inlet opening or the outlet opening. To this end the longitudinal side 33 is executed with an external thread (not shown) and the respective opening in the form of an internal thread (not shown). Alternatively the closure device of the invention may be realized as a bolt having a securing element for closing the respective opening, i.e., the inlet or outlet opening by means of the bolt. Moreover the closure device of the invention may be configured as a different releasable closure member.

In accordance with the invention, the sensor 41 of sensor device 40 generally is a sensor adapted to detect operation parameters of the lubricant such as, e.g., the temperature, the water content in the lubricant or humidity of the lubricant, through immersion in the lubricant bath at the closure device 20 inserted in the housing part, due to the circumstance that the first end surface 31$a$ of the first end portion 31 is in contact with the lubricant. The first end surface 31$a$ here is part of the sensor 41 and is adapted for detecting the respective operation parameter or operational condition of the lubricant.

In order to detect the water content in the lubricant, the sensor 41 may be realized as an impedance or capacitor K. Fundamentally, in accordance with the invention any kind of impedance/capacitor in is conceivable in which the dielectric (the permittivity) on the sensor is influenced by the substance to be detected, i.e., the lubricant. The capacitor K may in particular be realized as a plate capacitor, cylinder capacitor, surface capacitor, i.e. with adjacent tracks such as, e.g., interdigital structures or finger structures. The end surface 31$a$ may in particular be formed of two capacitor plates or generally capacitor parts in order to detect the effect of the dielectric properties of the lubricant in accordance with the impedance/capacitance measurement principle. The end surface 31$a$ may also have two capacitor parts. Alternatively, the first end surface 31$a$ or the sensor device 40, respectively, may consist of a planar capacitor KP or surface capacitor having two capacitor surfaces 36, 37 engaging each other in surface contact or in a fork-type configuration in order to maximize the size of the mutually facing boundary lines or boundary surfaces (FIG. 3$a$). The outwardly directed planar capacitor partial surfaces of the planar capacitor electrodes or planar capacitor partial plates 36, 37 extend in the end surface 31$a$. Between the planar capacitor electrodes 36, 37 a groove may be provided or an insulation material may be provided. Moreover the planar capacitor KP may be realized such that the planar capacitor partial surfaces thereof form a unified capacitor total surface as regards the surface contour line. The surface capacitor may in particular be realized by an arrangement of tracks extending along each other in portions thereof, wherein respective adjacent tracks constitute cooperating capacitor electrodes. The surface capacitor may in particular be realized with an interdigital structure or a finger structure. In another practical example, the capacitor parts may be realized as two antennae projecting from the first end surface 31$a$ (not represented in the figures).

The use of a surface capacitor in accordance with the invention is advantageous in the determination of the water content in viscous media, for an exchange of the medium can be performed better if it is not impeded, e.g., by passages or cavities.

In the realization of the sensor 41 as a capacitor K, it may in particular be provided in accordance with the invention that the capacitor surfaces or at least one of the capacitor surfaces and in particular portions thereof are coated with a special capacitor layer. This capacitor layer has the function of a protection of capacitor surfaces or regions thereof against electrical, chemical and/or mechanical influences and/or generally a passivation of the capacitor surfaces.

Figure 4:
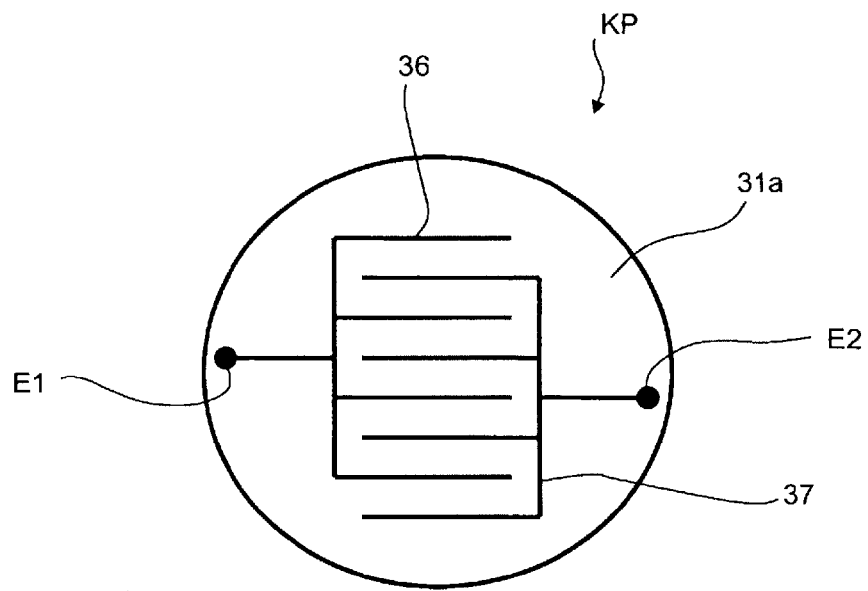
Figures 7A, 7B:
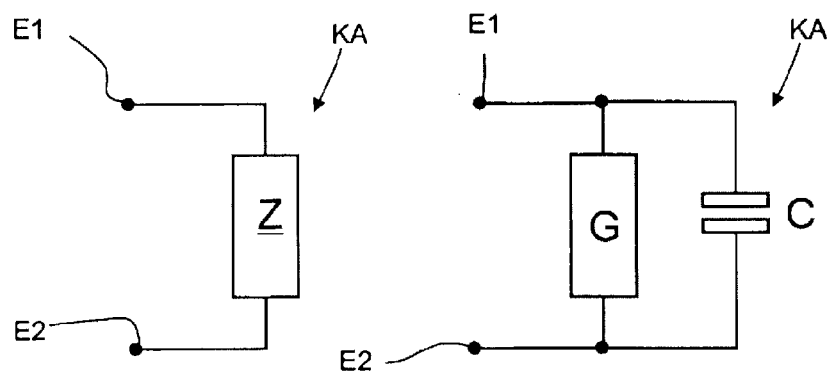
FIG. 7a is an equivalent circuit diagram for electrical driving of a plate capacitor represented in FIGS. 3, 5 and 6.
FIG. 7b is another equivalent circuit diagram for electrical driving of a plate capacitor represented in FIGS. 3, 5 and 6.

The power supply device E is used to apply AC voltage to the capacitor parts or to the capacitor plates of the respective capacitor provided or of the capacitor assembly KA. In order to represent the connection of the power supply device E to the respective capacitor electrodes, in the represented example to the planar capacitor electrodes 36, 37, contact locations E1 and E2 are drawn schematically for clarity in FIG. 4; these need, however, not be provided in a realization of the represented devices. In a measurement function an impedance is determined from the applied AC voltage, as is represented schematically in FIG. 7a showing an electric equivalent circuit diagram. The impedance of a capacitor is determined by its geometry and the electric properties of the dielectric placed between the capacitor plates. In general the impedance may be considered to be a complex resistance. In a general way, the impedance may be considered to be a complex resistance. Alternatively or additionally it may be provided that a capacitor provided in accordance with the invention and having an AC voltage applied thereto is used to measure an amplitude and/or a phase shift and/or an attenuation each presenting the measured AC voltage relative to the applied AC voltage in order to determine from this, e.g. in the sensor device or by means of the measurement function, a relative permittivity epsilon-r ($\in$r). In FIG. 7b an equivalent circuit diagram of a technical realization of an embodiment of a capacitor assembly KA provided in accordance with the invention and including a capacitor C and a resistor G connected in parallel with the latter is represented, which may be used to determine the mentioned measurement signals or measurement quantities. In the capacitor C the stored electric power is described, and in the parallel conductance G the conductivity.

Figure 5:
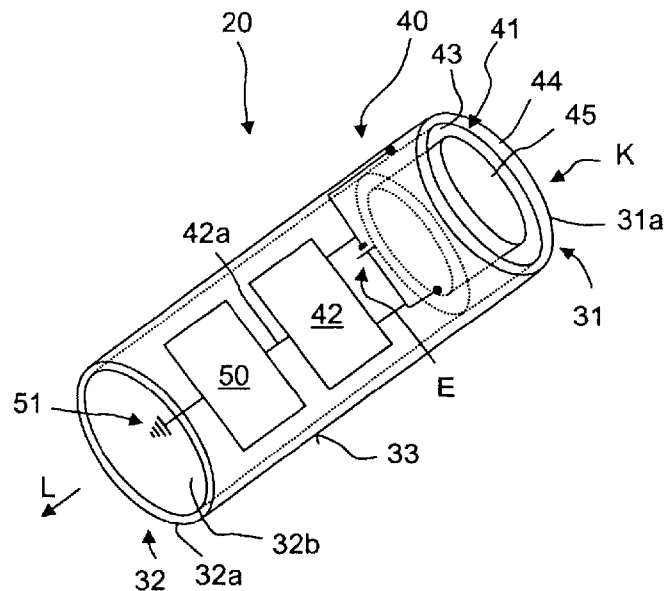
FIG. 5 is a schematic representation of a further practical example of a closure member provided in accordance with the invention and having an end portion implemented as a capacitor, into which a sensor device and a transceiver as well as a power supply for the capacitor are functionally integrated, wherein the capacitor is realized with ring-shaped capacitor surfaces.
Figure 6:
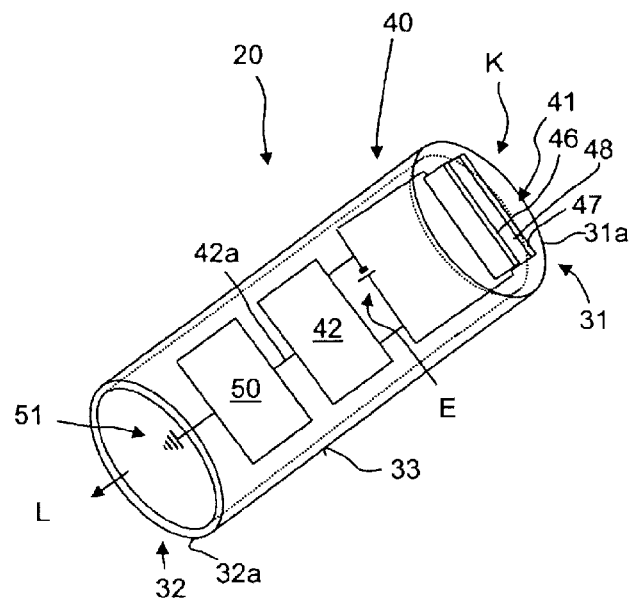
FIG. 6 is a schematic representation of a further practical example of a closure member provided in accordance with the invention and having an end portion implemented as a capacitor, into which a sensor device and a transceiver as well as a power supply for the capacitor are functionally integrated, wherein the capacitor is realized as a plate capacitor.

According to a further practical example of the invention, the capacitor K may be realized by forming a peripheral groove 43 in the end surface 31a, so that the end portion 31 is formed by a peripheral capacitor ring 44 at the outer margin of the first end surface 31a, and a capacitor die 45 formed within the latter (FIG. 5). The mutually facing surfaces of the capacitor ring 44 and of the capacitor die 45, i.e. the inner surface of the capacitor ring 44 and the outer surface of the capacitor die 45 form the mutually facing capacitor surfaces between which the lubricant is present whose water content or degree of humidity is to be measured with the aid of the capacitor K. Alternatively, the end portion 31 or the sensor 41, respectively, may also have the form of a plate capacitor having two capacitor plates 46, 47 extending, e.g., in parallel and from the first end surface 31a, and an interstice 48 located between these in accordance with FIG. 6.

According to a practical example of the invention, the sensor 41 is realized such as to be capable of detecting the water content at least in a range between 0% and 40% of relative humidity. The advantage of the sensors provided in accordance with the invention and in particular of the utilization of capacitors for determining the humidity is that it is possible to achieve such measurement ranges and required measurement accuracies.

In particular as a result of realizing the sensor in the form of a capacitor sensor having structurally realized capacitor plates, the very lubricating agent is used as a dielectric, or in the case of an embodiment comprising a capacitor layer, the lubricant in combination with the capacitor layer. The measurement signal is essentially determined by the relative permittivity. Lubricants have a relative permittivity $\in$r (epsilon-r) of approx. 2-5. Water on the other hand has, due to the innermolecular hydrogen bond, a relative permittivity $\in$r (epsilon-r) of approx. 80. It is therefore possible to discriminate between water and lubricating agent in terms of measurement technology, and to detect and ascertain the water content in lubricants.

The capacitor layer in its function of a protective layer serves as a protection of capacitor surfaces or regions thereof against electrical, chemical and/or mechanical influences in particular owing to the lubricant in the operation of the component in which the capacitor is integrated.

The passivation function of the capacitor layer is furthermore achieved by reducing a parallel conductance value through water, reduction of the risk of soiling of the capacitor surfaces, and prevention of a short-circuit between the electrodes by metal abrasion or by the detachment of metallic parts inside the transmission mechanism.

The capacitor layer is applied as a relatively thin layer having a low permittivity number and in particular a permittivity number as low as possible, or low relative permittivity or low dielectric constant.

The protective layer or insulation layer may in particular be formed of a Si oxide and/or a Si nitride and/or aluminum oxide and/or parylene and/or a polymer material, wherein the material for the formation of the protective layer may be applied over the full surface or in areas on the sensor surfaces or the active sensor area. Here it may in particular be provided, in order to realize a passivation function, that the protective layer is arranged on the surface of only one electrode and there over the entire surface or a region thereof.

In accordance with one embodiment of the invention, the coating is formed by vapor deposition or sputtering of an insulator. In particular the material of the insulator may in particular contain SiO, SiO2 or be comprised of SiO, SiO2 exclusively. The thickness of the insulation layer is in particular between 100 nm and 1000 nm. The permittivity number $\in_r$ may be in the range between 1.5 and 5.0 and in particular between 1.9 and 2.3.

In accordance with the invention, application of the insulator on one electrode or both electrodes may also be effected by sputtering such as, e.g., by a chemical vapour deposition (CVD) method. As the material for producing the insulation layer on the capacitor surface it is in particular possible to use SiO2 (silicon dioxide) and/or Si3N4 (silicon nitride), so that the insulation layer is then formed, or comprised, of one or both of these materials. In this production of the insulation layer, a layer thickness of d=100 nm to 1000 nm is preferably provided. The permittivity number $\in_r$ may be situated in the range between 1.5 and 2.5 and in particular between 2.0 and 5.0.

In a further alternative, the coating of capacitor surface may be executed, e.g., as parylene through polymer coating from a gas phase. For producing the insulation layer a layer thickness of d=10 μm to 51 μm is provided. The permittivity number $\in_r$ may be situated in the range between 2.0 and 4.0 and in particular between 2.6 and 3.2.

The sensor device 40 may in particular comprise a signal processing device 45 functionally communicated with the sensor 41, which detects the electric signals of the sensor. The signal processing device 45 may also include a comparison function which compares the detected sensor signals corresponding, depending on the sensor, to a humidity content, and optionally a pressure and/or a temperature, to a limit value or to several limit values, and which generates an output signal which corresponds to and indicates that the sensor signal is below a limit value, exceeds a limit value, or is situated between two limit values, and displays this.

The sensor device 40 and in particular the signal processing device 45 may be functionally communicated with the transceiver 51 for receiving the sensor signals and/or the output signals from the sensor device and for the signal transmission of the sensor signals to an external reception unit via a connecting line 45a. To this end, the transceiver 51 is connected to a signal transmission device 52. According to the practical examples represented in FIGS. 3, 5 and 6, the signal transmission device 52 has the form of an antenna for the transmission of signals and information by wireless and thus in a cordless manner to an external reception unit, to which in turn a signal processing device for further processing and in particular for evaluating the necessity of maintenance measures is coupled. Alternatively, the signal transmission device 52 may be realized with a wire or cable connection to the external reception unit.

The external reception unit is a unit externally of the closure device, and in particular a unit externally of the housing comprising the housing part 20 of the invention. Here the external reception unit may be part of a hand-held maintenance apparatus H.

This cordless implementation of the signal connection between the transceiver 51 and an external processing device or external maintenance device results in a particularly simple and compact construction, for additional cabling is saved, and in case a sensor or a transceiver should malfunction, it would be sufficient to simply replace the closure device 20 having the deficient sensor/transceiver with a closure device 20 having a functional sensor/transceiver, without having to release or fasten further plug connections.

The transceiver 51 may be arranged in a recess of a second end portion 32 of the closure device 20 having the form of a head end and disposed opposite from the first end portion 31, wherein the second end portion 32 of the closure device has an outer side 32a forming an outer side of the housing part 10, 30 when the closure device is in the condition closing the housing part 10, 30, and wherein an inner range of the outer side of the second end portion of the closure device has an opening 32b of the recess for wireless transmission of the sensor signal to an external reception unit. Here a resin layer having transmissibility for the wireless transmission waves may be inserted in the opening 32b. The outer side of the second end portion 32 of the closure device having the opening may also be covered entirely or partially by a resin layer.

Figure 8A:
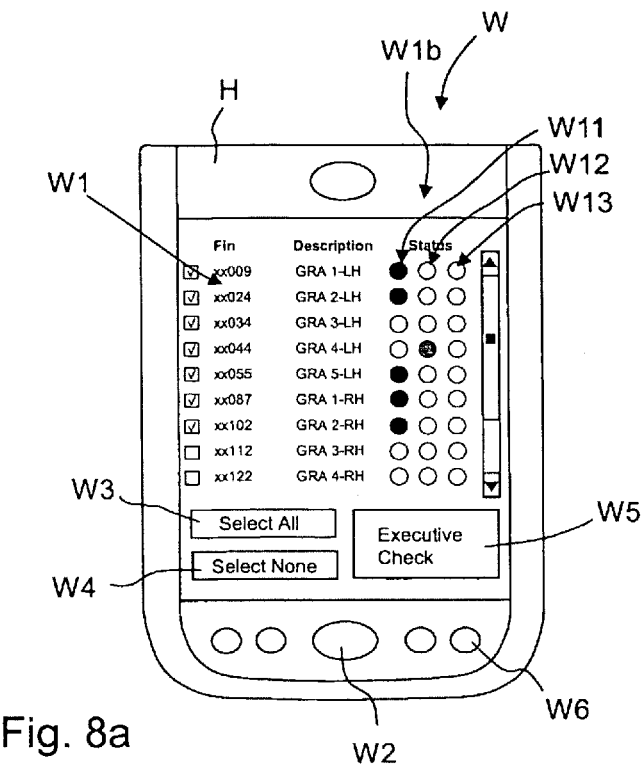
FIG. 8a shows a practical example of a maintenance device usable for the diagnostic system of the invention or the diagnosing method of the invention, which is realized as a hand-held apparatus, with a practical example of a diagnostic display.
Figure 8B:
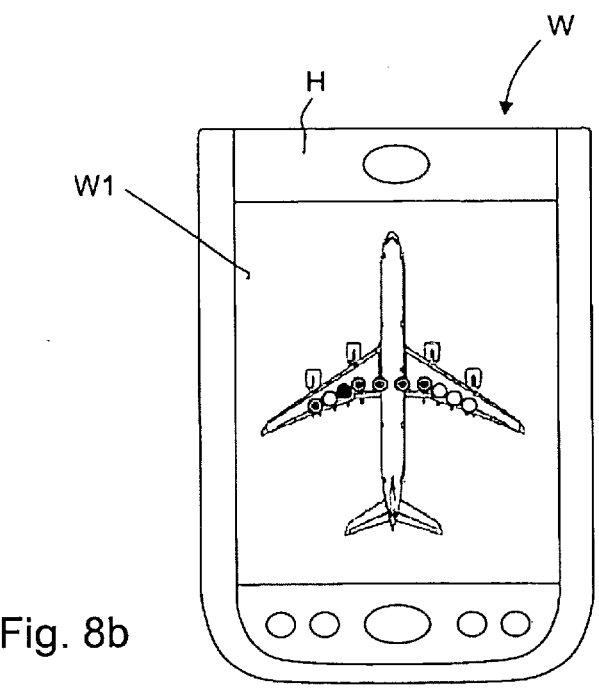
FIG. 8b shows, as compared with the display options represented in FIGS. 6a and 6b, a further practical example of a diagnostic display for a maintenance device usable for the diagnostic system of the invention or the diagnosing method of the invention and realized as a hand-held apparatus, wherein the display contents represented by way of example are intended for use in the maintenance of an aircraft.

It is particularly advantageous if housing parts according to the invention and having movable parts that are bathed in a lubricant are monitored by a cordless diagnostic system as illustrated, by way of example, in FIGS. 8a and 8b.

FIGS. 8a and 8b each show a hand-held apparatus as a practical example of an external processing device or external reception and/or transmission device for a cordless diagnostic system having integrated therein a processing unit for receiving and processing sensor signals which are detected by the sensors 41 in a housing part 10 of the invention and emitted by the associated transceivers, as well as a display means. On the display means in FIG. 8b the example of an aircraft is used in order to visualize the utilization of several housing parts 10 of the invention which are installed in certain positions on the wings of the aircraft which are illustrated by respective circles.

The sensors situated in the closure devices 20 of housing parts of the invention that are employed on the aircraft emit sensor signals to the transceivers 51 which are equally integrated in the closure devices 20 of the housing parts, which in turn transmit them to the external processing unit. The processing unit recognizes the housing part of origin of a sensor signal and displays this on the display means of the hand-held apparatus. In addition the processing unit evaluates the arriving sensor signals in order to draw conclusions concerning the condition of the lubricant in the respective housing parts and display diagnostic information as shown, e.g., in FIG. 6a.

The separate maintenance device W may in particular comprise a transceiver for receiving sensor signals from the transceiver 51 associated to the sensor device 40, wherein the maintenance device includes a processing function for determining, based on the sensor signal, a value for the operational condition of a lubricant present in the housing part. The separate maintenance device W may also, e.g. due to a corresponding input thereto, generate a control command which is transmitted via the transceiver 51 of the closure device 20 to the sensor device 40 and which activates the sensor device 40 to perform a measurement.

The maintenance device W may comprise a display device W1 for displaying the sensor quantities and/or determined maintenance information. A practical example of a display format that may be represented by means of the display device may include: an area W1a showing a definition or indication of at least one respective queried or displayed sensor and/or at least one component in which the respective sensor is installed, and an area W1b in which the technical status of the respective displayed sensor is shown. As is furthermore shown schematically in FIG. 8a, the display format may be such that different sensors 41 or sensor devices 40 or components such as actuators, for instance, in which these are installed, are listed in a row form and, for example, laterally to the right from them three evaluation columns W11, W12, W13 having, e.g., the form of three display options that may be marked and are arranged side by side in the same row and, e.g., luminous indicators are provided, which is represented only schematically in FIG. 8a. Marking or non-marking of fields within one respective row may thus be provided for one closure device each or for an apparatus having one or several closure devices, with the following meanings with regard to required maintenance measures:

marking of a field of the first column: no need to replace the lubricant, for the measured water content or the measured relative humidity in the lubricant container is below a first predetermined limit value;

marking of a field of the first column and additional marking of a field of the third column: no need to replace the lubricant, for although the measured water content or the measured relative humidity in the lubricant container is higher than the first predetermined limit value, it is nevertheless below a second predetermined limit value, but the necessity of replacing the lubricant must be monitored because replacing the lubricant may become necessary within a foreseeable period of time;

marking of a field of the second column: there is no sufficiently good signal quality in the transmission of signals or data between the maintenance device and the sensor devices 40 or components in question, and particularly the respective selected ones in which the respective selected sensor device 40 is installed;

marking of a field of the third column: replacement of the lubricant is required, for the measured water content or the measured relative humidity in the lubricant container is higher than the second predetermined limit value;

marking of none of the fields of the columns in a row: no query was performed by means of the maintenance device W.

In the representation of FIG. 8a, some of the circular fields are tinted in grey. This is to give a schematic exemplary indication of the lubricant conditions detected at various sensor devices, depending on which fields of a respective row belonging to a sensor device are marked, i.e., tinted in grey in FIG. 8a.

In particular it may be provided that the first limit value is in the range between 6% and 10% and the second limit value in the range between 12% and 16%.

The layout of fields may be realized in the display format such that one field each that can be marked is arranged in one respective column of a row. The respective field may have a circular shape, for example. The respective field associated to a row and a column may be realized as an area within a unified display area of, e.g., an LCD display area or as a lamp or separate luminous indicator.

In addition it may be provided that the fields of respective different columns are represented in different colors or assume different colors and/or are illuminated in different colors if they are to be marked or accentuated, for instance as the result of a query. For example it may be provided that the fields of the first column turn green, the fields of the second column turn yellow, and the fields of the third column turn red if they are to be marked or displayed.

For a corresponding realization of these checking functions in one of the practical examples according to the invention, the sensor device may include a function including a comparison function in which two limit values are stored or whereby two limit values are predetermined. The first limit value may be a value defined between 6% and 10% of relative humidity, and the second limit value may be a value defined between 12% and 16% of relative humidity. For example, the first limit value may be equal to 8%, and the second limit value may be equal to 12%. In this practical example the sensor device and/or the maintenance device W may be executed such that the detected measurement signal is supplied to the comparison function, with the comparison function determining in which one of the ranges delimited by the two limit values the respective detected signal value is situated (either below the first limit value or between the two limit values or above the second limit value), so that marking of the field in the corresponding column of the display format takes place on the basis of the identification of a range defined by the limit values. Hereby the urgency of a maintenance measure may be evaluated and displayed for the three ranges in accordance with one of the kinds presently described.

The method of the invention may generally be realized as a diagnosing method for monitoring a lubricant medium by means of a sensor device and a maintenance device associated thereto. In this case a measurement signal detected by a sensor device is supplied to a comparison function, with the comparison function comparing the respective detected measurement signal to two limit values and identifying based on this comparison whether the respective detected signal value is situated in a first range below a first limit value or in a second range between the first and a second limit value greater than the first limit value, or in a third range above the second limit value. As a result of the identification of a range for the respective detected signal value, marking of one of three fields associated to a respective one of the ranges is effected in a display format of a display device.

In the diagnosing method it may be provided that the first limit value is a value for the relative humidity that is situated between 6% and 10%, and that the second limit value is a value for the relative humidity that is situated between 12% and 16%.

Alternatively or additionally it may be provided in the diagnosing method that in accordance with the display format of a display device for one respective sensor device whereby the measurement signal was detected, three fields each are associated to that sensor device, of which one field each is arranged in one of three columns of the display format, with the following meanings:

marking of a field of the first column means that the detected measurement signal is below the first predetermined limit value;

marking of a field of the first column and additional marking of a field of the third column means that the detected measurement signal is situated between the first predetermined limit value and the second predetermined limit value;

marking of a field of the second column means that there is no sufficiently good signal quality in the transmission of signals or data between the maintenance device and the respective, and particularly selected, sensor devices or the respective transceivers associated to them;

marking of a field of the third column means that the detected measurement signal is above the second predetermined limit value;

marking of none of the fields of the columns in a row means that no query was performed by means of the maintenance device W.

Marking of fields may be done with the aid of a multifunctional switch W2. Moreover the maintenance device W or the hand-held apparatus H may comprise a switch W3 for selecting all drivable sensors or sensor devices ("select all"). Moreover a switch W4 may be provided whereby selecting sensors or sensor devices may be precluded ("select none"). Moreover a switch W5 may be provided whereby in one or several ones of respective selected sensors or sensor devices of the maintenance device W an activation signal may be sent to these sensors or sensor devices, so that a measurement is carried out by these and/or a measurement value or signal value stored there is read out by them and sent to the sensors or sensor devices.

It may furthermore be provided that, for instance with the aid of a further switch W6, the installation locations of sensors or sensor devices on the system or vehicle for which the maintenance device is being used are displayed. In FIG. 8b such a display is represented for a case in which the maintenance system and the sensor device of the invention is employed for an aircraft. In this embodiment, in which a satellite position determination sensor is integrated on one or several sensor devices and more specifically closure devices 20, an association of the respective sensor device may be effected by means of the determined position of the respective sensor device. This may be performed in addition or alternatively to the transmission of an address ID of the respective sensor device queried for a sensor value.

Accordingly, the maintenance device W may comprise a function module whereby a value for an operational condition of a lubricant present in the housing part may be determined from a sensor signal, and whereby the maintenance information required for a maintenance task may be transmitted to a display means and displayed with the aid of the display means.

Here it is particularly advantageous if the diagnostic system sensor transmits signals originating from different sensors that are mounted in one and the same housing part (e.g., in the inlet opening and in the outlet opening) to the processing unit and there compares them to each other, wherein a comparison function value is formed as the result of the comparison and underlaid the further processing. Thus it might be possible, e.g., to form a mean value of two sensor signals originating from one and the same housing part, or the smaller one of the two sensor signals would be discarded as a general rule. The latter option would, for instance, be a particularly simple and effective manner of proceeding for cases where one of the sensors in the inlet or outlet opening of the housing part is faulty and supplies a much too low sensor signal or no sensor signal at all.

Furthermore it is advantageous if the external processing unit compares the signals received from a sensor assembly group to predetermined limit values for these signals and visualizes on the display whether the received signal is situated within predetermined limit values for the signal (FIG. 8a).

For the case that a received sensor signal lies outside the range of the predetermined limit values, the processing unit may output a warning signal, in particular an acoustic or visual warning signal.

It is readily evident to the person having skill in the art that the principle of the diagnostic system illustrated by way of example in FIGS. 8a and 8b may be used with the maintenance device H and diagnosing method carried out thereby, also for assisting the maintenance of any kind of land, air, water or underwater vehicles. This is on the condition that a sensor means for generating and/or storing sensor signals is provided on at least one examination location for the diagnosis of faults on high-maintenance housing parts of the vehicle, wherein the sensor signals are transmitted to a processing unit and the processing unit is operatively connected to a display means for displaying the sensor signals and/or the determined diagnostic information. In this case the sensors and transceivers are integrated into closure members for closing inlet/outlet openings for lubricant in a housing part having movable components in the body of the vehicle, and the transceiver in the closure member of the housing part transmits the sensor signals from the housing part to the processing unit.

The invention claimed is:

1. A diagnostic system for detecting and transmitting a sensor value concerning an operational condition of a system component to an external reception and/or transmission device, the diagnostic system comprising:
    at least one sensor device comprising at least one sensor for generating sensor values corresponding to the respective first operational condition,
    a control device comprising a timer and a function for the performance of measurements by the sensor device at predetermined points of time or within predetermined time intervals,
    a signal transmission device for receiving the sensor signals from the sensor device and for signal transmission of the sensor signals of the sensor device to an external reception and/or transmission device,
    a power supply device for supplying electric energy to the sensor device and to the signal transmission device,
    wherein
    the diagnostic system comprises a device for the determination of a second operational condition of the system component, and
    the control function is configured such that at the predetermined points of time or at the predetermined time intervals at which it performs a detection of the second operational condition of the transmission mechanism, the control function compares generated sensor values corresponding to the respective second operational condition to a predetermined comparative value and only provides the sensor value corresponding to the respective second operational condition to the signal transmission device if it is higher or lower than this comparative value.

2. The diagnostic system according to claim 1, wherein the system component comprises a transmission mechanism having a housing, and the sensor device comprises a sensor for the determination of the water content of the lubricant contained in the container of the transmission mechanism.

3. The diagnostic system according to claim 1, wherein the device for the determination of a second operational condition of the system component comprises a temperature sensor which measures the temperature in the housing and/or in the surroundings of the housing, and/or a pressure sensor which measures the pressure in the housing and/or in the surroundings of the housing.

4. The diagnostic system according to claim 1, wherein the transmission and reception module is adapted to be switched between a standby mode and a transmission mode, and wherein it comprises: an antenna device, a querying function for querying the signal strength present at the antenna device at predetermined points of time, a comparison function for determining that the detected signal strength present at the antenna device is higher than a predetermined limit value, and depending on this, generation of an activation signal to the transmission commanding function and a transmission commanding function for activating the antenna device for the reception and the transmission of signals between the signal transmission device and the external reception and/or transmission device, and
    wherein the transmission and reception module is configured such that due to the activation of the transmission mode it generates signals for the sensor values detected by the sensor and transmits them to the antenna device for transmission to the external reception and/or transmission device.

5. The diagnostic system according to claim 1, wherein the maximum transmitting power furnished by the signal transmission device is adjusted or may be adjusted by the control function of the signal processing device on the basis of a predetermined value or may be adjusted by the external reception and/or transmission device.

6. A diagnosing method for detecting and transmitting a sensor value concerning an operational condition of a system component to an external reception and/or transmission device, comprising:
    generating sensor signals corresponding to a respective first operational condition of the system component,
    performing measurements by the sensor device at predetermined points of time or at predetermined time intervals,
    determining a second operational condition of the system component,
    at the predetermined points of time or at the predetermined time intervals, detecting the second operational condition of the transmission mechanism and comparing it to a predetermined comparative value,
    furnishing the sensor value corresponding to the respective first operational condition to the signal transmission device only if it is higher or lower than this comparative value.

* * * * *